(12) United States Patent  
Rofougaran

(10) Patent No.: US 8,489,199 B2  
(45) Date of Patent: Jul. 16, 2013

(54) BIO-MEDICAL UNIT WITH POWER HARVESTING MODULE AND RF COMMUNICATION

(75) Inventor: Ahmadreza (Reza) Rofougaran, Newport Coast, CA (US)

(73) Assignee: Broadcom Corporation, Irvine, CA (US)

( * ) Notice: Subject to any disclaimer, the term of this patent is extended or adjusted under 35 U.S.C. 154(b) by 519 days.

(21) Appl. No.: 12/783,649

(22) Filed: May 20, 2010

(65) Prior Publication Data

US 2011/0077714 A1 Mar. 31, 2011

Related U.S. Application Data

(60) Provisional application No. 61/247,060, filed on Sep. 30, 2009.

(51) Int. Cl.
*A61N 1/378* (2006.01)

(52) U.S. Cl.
USPC .............................................. 607/60; 607/61

(58) Field of Classification Search
USPC .................... 607/30, 32, 33, 60, 61
See application file for complete search history.

(56) References Cited

U.S. PATENT DOCUMENTS

| 7,125,382 B2 | 10/2006 | Zhou et al. |
| 7,241,266 B2 | 7/2007 | Zhou et al. |
| 7,266,269 B2 | 9/2007 | Koste et al. |

OTHER PUBLICATIONS

Arjang Hassibi, et al., "A Spectral-Scanning Nuclear Magnetic Resonance Imaging (MRI) Transceiver", IEEE Journal of Solid-State Circuits, Jun. 2009, pp. 1805-1813, vol. 44, No. 6.

John E. Speich, et al., "Medical Robotics", Encyclopedia of Biomaterials and Biomedical Engineering, 2004, pp. 983-992, Marcel Dekker, Inc.

Eric Freudenthal, et al., "Evaluation of HF RFID for Implanted Medical Applications", Apr. 16, 2006, 4 pp.

Gibson, Ultrasound as a Proposed Drug Release Mechanism in Biomedical Microrobots, Arizona Space Grant Consortium, Univ. of Arizona Advanced Microsystems Laboratory, Dept. of Aerospace and Mechanical Engineering, Apr. 19, 2008, 17 pages.

Marin Soljacic et al., "WiTricity: Non-Radiactive Wireless Power Transfer," Oct. 9, 2008, 56 pages.

Robert E. Carlson, Ph.D., et al., "Development of an Implantable Glucose Sensor," Dec. 4, 2007, 16 pages.

Shekhar Bhansali, "Role of MEMS and Nanotechnology in Medical Technologies," University of South Florida, Mar. 1, 2004, 29 pages.

*Primary Examiner* — Carl H Layno
*Assistant Examiner* — Paula J Stice
(74) *Attorney, Agent, or Firm* — Garlick & Markison

(57) ABSTRACT

A bio-medical unit includes a power harvesting module and an RF communication module. The power harvesting module generates a power supply voltage from the electromagnetic signal. The RF communication module interprets a predetermined pattern of the transmitting of the electromagnetic signal to determine null intervals; receives a downstream RF communication signal during at least one of the null intervals; converts the downstream RF communication signal into downstream information; converts upstream information into an upstream RF communication signal; and/or transmits the upstream RF communication signal during one or more of the null intervals.

20 Claims, 27 Drawing Sheets

BIO-MEDICAL UNIT WITH POWER HARVESTING MODULE AND RF COMMUNICATION

This patent application is claiming priority under 35 USC §119 to a provisionally filed patent application entitled BIO-MEDICAL UNIT AND APPLICATIONS THEREOF, having a provisional filing date of Sep. 30, 2009, and a provisional Ser. No. 61/247,060.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Technical Field of the Invention

This invention relates generally to medical equipment and more particularly to wireless medical equipment.

2. Description of Related Art

As is known, there is a wide variety of medical equipment that aids in the diagnosis, monitoring, and/or treatment of patients' medical conditions. For instances, there are diagnostic medical devices, therapeutic medical devices, life support medical devices, medical monitoring devices, medical laboratory equipment, etc. As specific exampled magnetic resonance imaging (MRI) devices produce images that illustrate the internal structure and function of a body.

The advancement of medical equipment is in step with the advancements of other technologies (e.g., radio frequency identification (RFID), robotics, etc.). Recently, RFID technology has been used for in vitro use to store patient information for easy access. While such in vitro applications have begun, the technical advancement in this area is in its infancy.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE SEVERAL VIEWS OF THE DRAWING(S)

DETAILED DESCRIPTION OF THE INVENTION

Figure 1:
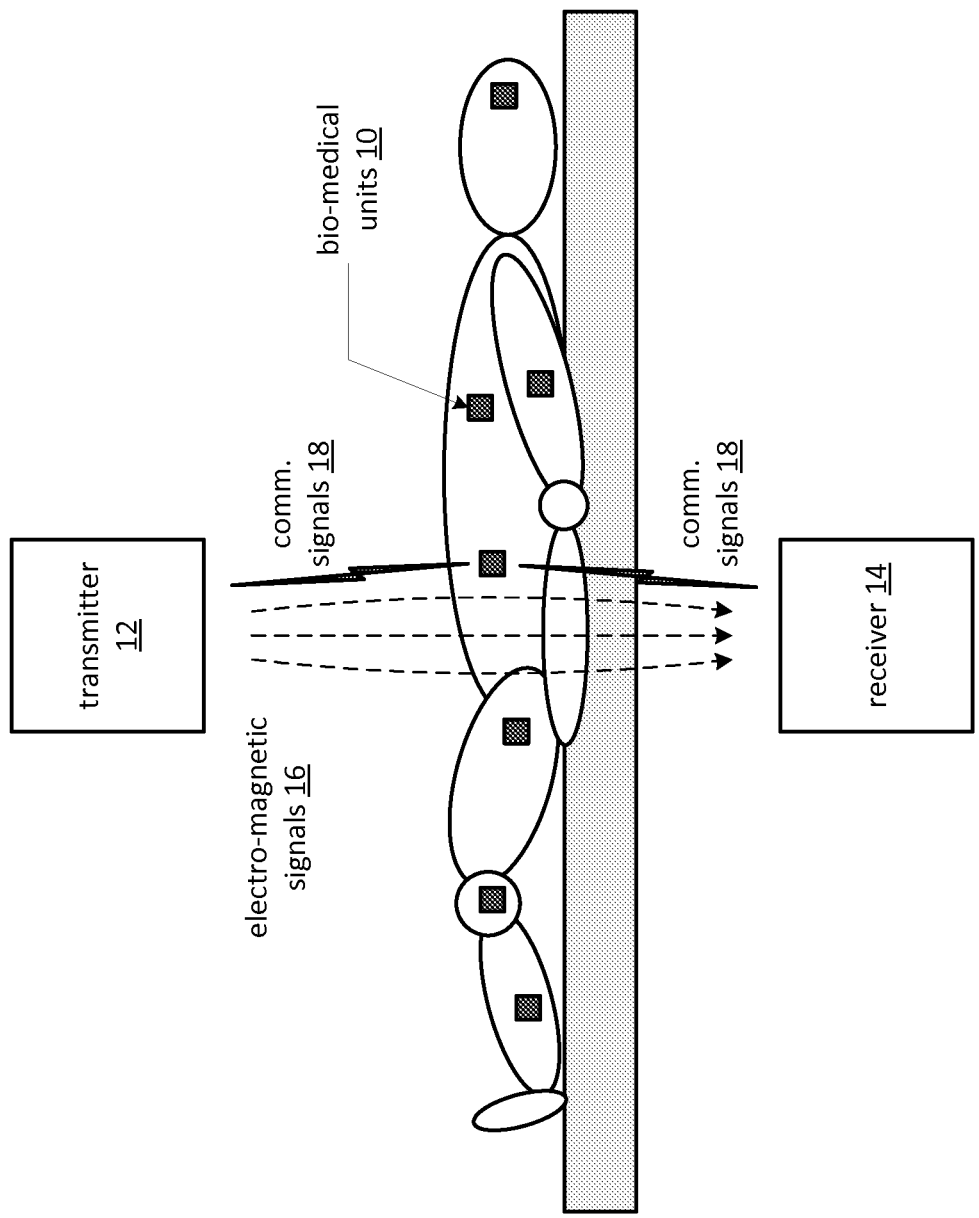
FIG. 1 is a diagram of an embodiment of a system in accordance with the present invention.

FIG. 1 is a diagram of an embodiment of a system that includes a plurality of bio-medical units 10 embedded within a body and/or placed on the surface of the body to facilitate diagnosis, treatment, and/or data collections. Each of the bio-medical units 10 is a passive device (e.g., it does not include a power source (e.g., a battery)) and, as such, includes a power harvesting module. The bio-medical units 10 may also include one or more of memory, a processing module, and functional modules. Alternatively, or in addition to, each of the bio-medical units 10 may include a power source.

In operation, a transmitter emits 12 electromagnetic signals 16 that pass through the body and are received by a receiver 14. The transmitter 12 and receiver 14 may be part of a piece of medical diagnostic equipment (e.g., magnetic resonance imaging (MRI), X-ray, etc.) or independent components for stimulating and communicating with the network of bio-medical units in and/or on a body. One or more of the bio-medical units 10 receives the transmitted electromagnetic signals 16 and generates a supply voltage therefrom. Examples of this will be described in greater detail with reference to FIGS. 8-12.

Embedded within the electromagnetic signals 16 (e.g., radio frequency (RF) signals, millimeter wave (MMW) signals, MRI signals, etc.) or via separate signals, the transmitter 12 communicates with one or more of the bio-medical units 10. For example, the electromagnetic signals 16 may have a frequency in the range of a few MHz to 900 MHz and the communication with the bio-medical units 10 is modulated on the electromagnetic signals 16 at a much higher frequency (e.g., 5 GHz to 300 GHz). As another example, the communication with the bio-medical units 10 may occur during gaps (e.g., per protocol of medical equipment or injected for communication) of transmitting the electromagnetic signals 16. As another example, the communication with the bio-medical units 10 occurs in a different frequency band and/or using a different transmission medium (e.g., use RF or MMW signals when the magnetic field of the electromagnetic signals are dominate, use ultrasound signals when the electromagnetic signals 16 are RF and/or MMW signals, etc.).

One or more of the bio-medical units 10 receives the communication signals 18 and processes them accordingly. The communication signals 18 may be instructions to collect data, to transmit collected data, to move the unit's position in the body, to perform a function, to administer a treatment, etc. If the received communication signals 18 require a response, the bio-medical unit 10 prepares an appropriate response and transmits it to the receiver 14 using a similar communication convention used by the transmitter 12.

Figure 2:
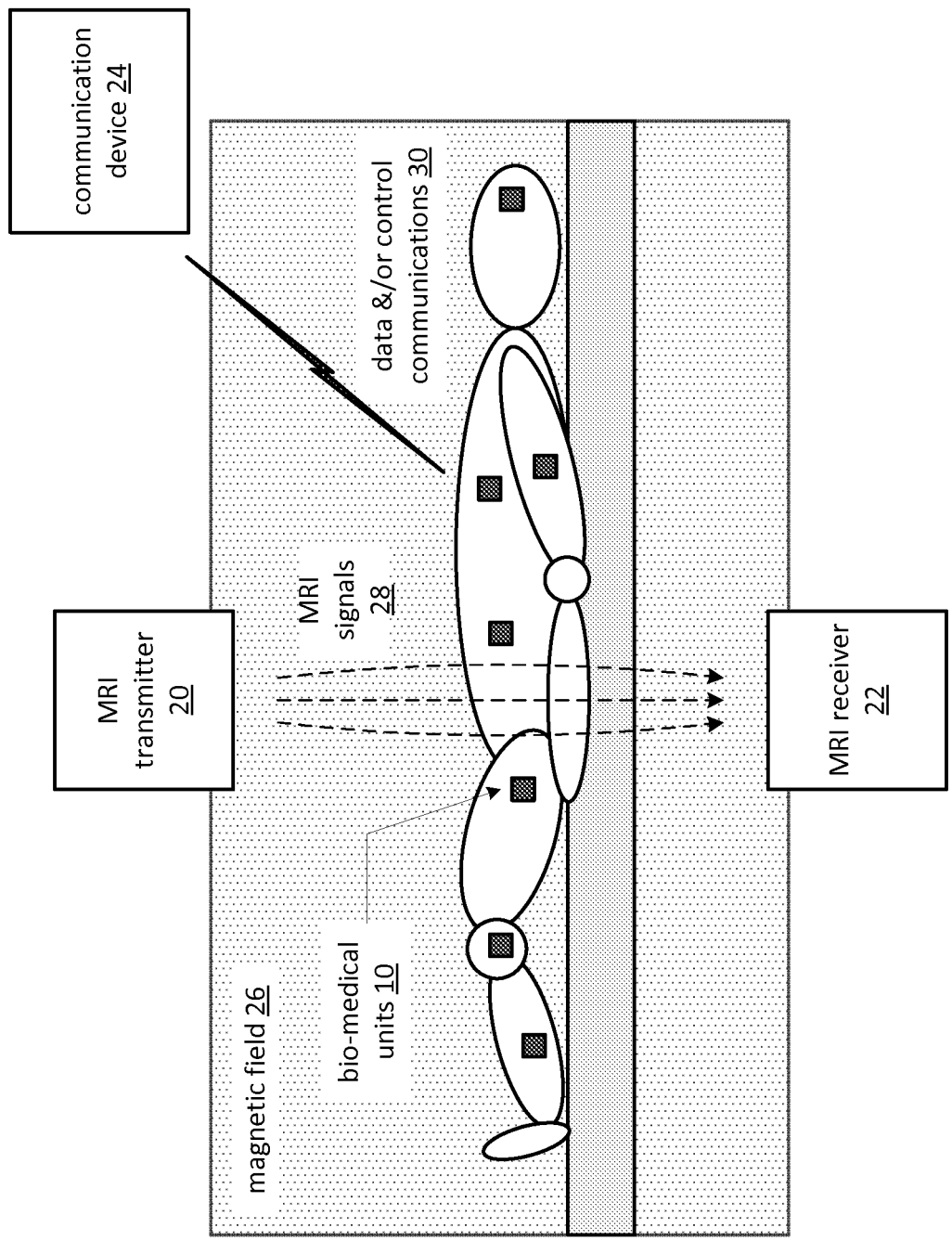
FIG. 2 is a diagram of another embodiment of a system in accordance with the present invention.

FIG. 2 is a diagram of another embodiment of a system that includes a plurality of bio-medical units 10 embedded within a body and/or placed on the surface of the body to facilitate diagnosis, treatment, and/or data collections. Each of the bio-medical units 10 is a passive device and, as such, includes a power harvesting module. The bio-medical units 10 may also include one or more of memory, a processing module, and functional modules. In this embodiment, the person is placed in an MRI machine (fixed or portable) that generates a magnetic field 26 through which the MRI transmitter 20 transmits MRI signals 28 to the MRI receiver 22.

One or more of the bio-medical units 10 powers itself by harvesting energy from the magnetic field 26 or changes thereof as produced by gradient coils, from the magnetic fields of the MRI signals 28, from the electrical fields of the MRI signals 28, and/or from the electromagnetic aspects of the MRI signals 28. A unit 10 converts the harvested energy into a supply voltage that supplies other components of the unit (e.g., a communication module, a processing module, memory, a functional module, etc.).

A communication device 24 communicates data and/or control communications 30 with one or more of the bio-medical units 10 over one or more wireless links. The communication device 24 may be a separate device from the MRI machine or integrated into the MRI machine. For example, the communication device 24, whether integrated or separate, may be a cellular telephone, a computer with a wireless interface (e.g., a WLAN station and/or access point, Bluetooth, a proprietary protocol, etc.), etc. A wireless link may be one or more frequencies in the ISM band, in the 60 GHz frequency band, the ultrasound frequency band, and/or other frequency bands that supports one or more communication protocols (e.g., data modulation schemes, beamforming, RF or MMW modulation, encoding, error correction, etc.).

The composition of the bio-medical units 10 includes non-ferromagnetic materials (e.g., paramagnetic or diamagnetic) and/or metal alloys that are minimally affected by an external magnetic field 26. In this regard, the units harvest power from the MRI signals 28 and communicate using RF and/or MMW electromagnetic signals with negligible chance of encountering the projectile or missile effect of implants that include ferromagnetic materials.

Figure 3:
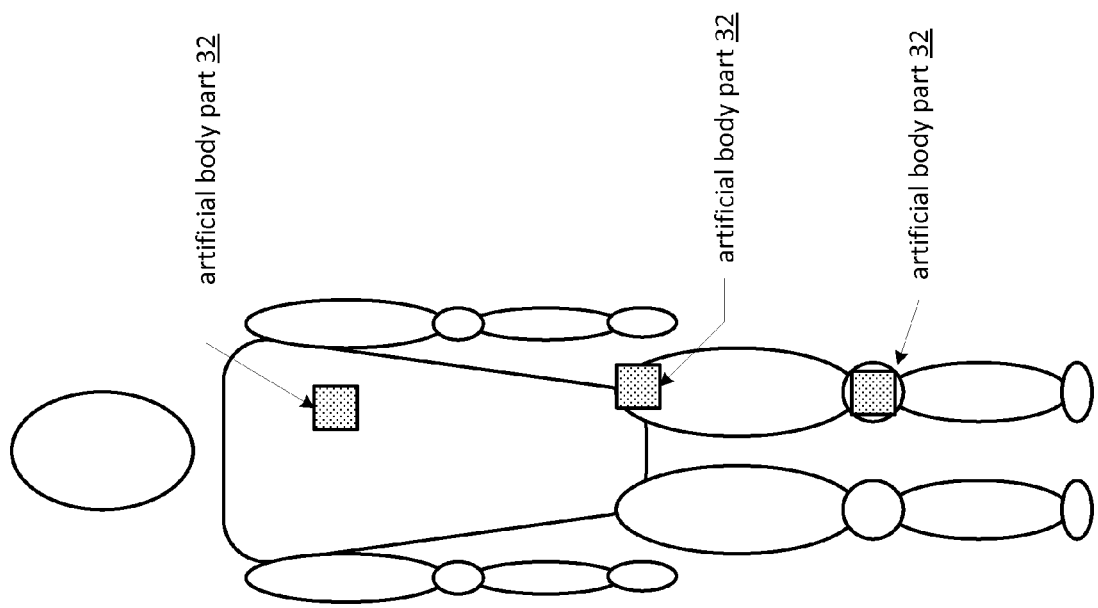
FIG. 3 is a diagram of an embodiment of an artificial body part including one or more bio-medical units in accordance with the present invention.

FIG. 3 is a diagram of an embodiment of an artificial body part 32 including one or more bio-medical units 10 that may be surgically implanted into a body. The artificial body part 32 may be a pace maker, a breast implant, a joint replacement, an artificial bone, splints, fastener devices (e.g., screws, plates, pins, sutures, etc.), artificial organ, etc. The artificial body part 32 may be permanently embedded in the body or temporarily embedded into the body.

Figure 4:
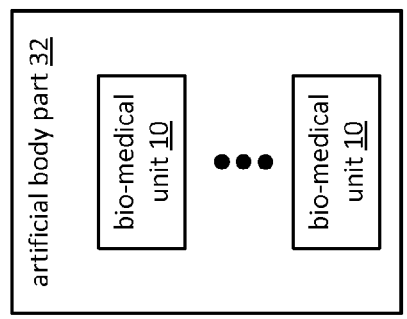
FIG. 4 is a schematic block diagram of an embodiment of an artificial body part in accordance with the present invention.

FIG. 4 is a schematic block diagram of an embodiment of an artificial body part system 32 that includes an artificial body part and one or more bio-medical units 10. The artificial body part (e.g., an electronic medical aid device (e.g., pacemaker, nerve stimulator, etc.), a metal artificial bone or portion thereof, a non-metal artificial bone or portion thereof, a metal screw, a non-metal screw, a metal plate, a non-metal plate, a metal splint, a non-metal splint, a metal suture, a non-metal suture, and/or an adhesive suture) includes a bio-medical mounting mechanism (e.g., a cavity, a surface mount area, etc.).

The bio-medical unit is mechanically associated with the artificial body part based on the bio-medical mounting mechanism. For example, if the artificial body part includes one or more cavities, the bio-medical unit 10 may positioned within the one or more cavities. As another example, if the artificial body part is an adhesive suture, the bio-medical unit 10 may be mounted on the surface of the suture and/or under a layer of the suture. As yet another example, if the artificial body part is molded, the bio-medical unit may be embedded within the artificial body part during the molding process.

The bio-medical unit includes a power harvesting module, a wireless communication module, and a functional module. The power harvesting module generates a supply voltage from a wireless source (e.g., MRI signals, magnetic fields, RF signals, MMW signals, etc.). The wireless communication module wirelessly communicates inbound data and outbound data with a communication device (e.g., device 24). One or more embodiments of the power harvesting module and/or of the wireless communication module are discussed with reference to one or more of the preceding and/or following Figures.

The functional module performs at least one function regarding the artificial body part, wherein the functional module performs the at least one function in response to the inbound data and/or to generate the outbound data. For example, the at least one function may include a treatment function, an adjustment function, a diagnostic function, a sampling function, and/or a monitoring function. As a more specific example, the treatment function may include applying a medication, applying a laser treatment, applying an ultrasound treatment, and/or applying an electronic stimulation treatment. As another more specific example, the adjustment function may include adjusting force of the artificial body part (e.g., adjusting tension of a splint) and/or adjusting torque of the artificial body part (e.g., turning a screw).

In an embodiment, the bio-medical unit further includes a coil and/or an antenna. The power harvesting module may use the coil to generate the supply voltage from electromagnetic energy and/or use the antenna to generate the supply voltage from RF signals and/or MMW signals. The wireless communication module may use the coil for near field communication and/or use the antenna for RF and/or MMW communication. Note that the coil and/or antenna may be at least partially embedded within the artificial body part (e.g., at least partially in a cavity, forming threads of a screw, etc.). Alternatively, or in addition to, the artificial body part functions as the at least one of the coil and the antenna. For example, a metal screw, plate, splint, etc. may be formed to provide the coil and/or antenna, or include a section of the artificial body part to provide the coil and/or antenna.

In a further embodiment of the artificial body part system 32 includes the artificial body part and a plurality of bio-medical units 10. The bio-medical units 10 may perform one or more functions. For example, a first bio-medical unit performs a treatment function; a second bio-medical unit performs an adjustment function; a third bio-medical unit performs a diagnostic function; a fourth bio-medical unit performs a sampling function; and a fifth bio-medical unit performs a monitoring function.

As another example, one bio-medical unit 10 may be used to detect infections, the body's acceptance of the artificial body part 32, measure localized body temperature, monitor performance of the artificial body part 32, and/or data gathering for other diagnostics. Another bio-medical unit 10 may be used for deployment of treatment (e.g., disperse medication, apply electrical stimulus, apply RF radiation, apply laser stimulus, etc.). Yet another bio-medical unit 10 may be used to adjust the position of the artificial body part 32 and/or a setting of the artificial body part 32. For example, a bio-medical unit 10 may be used to mechanically adjust the tension of a splint, screws, etc. As another example, a bio-medical unit 10 may be used to adjust an electrical setting of the artificial body part 32.

Figure 5:
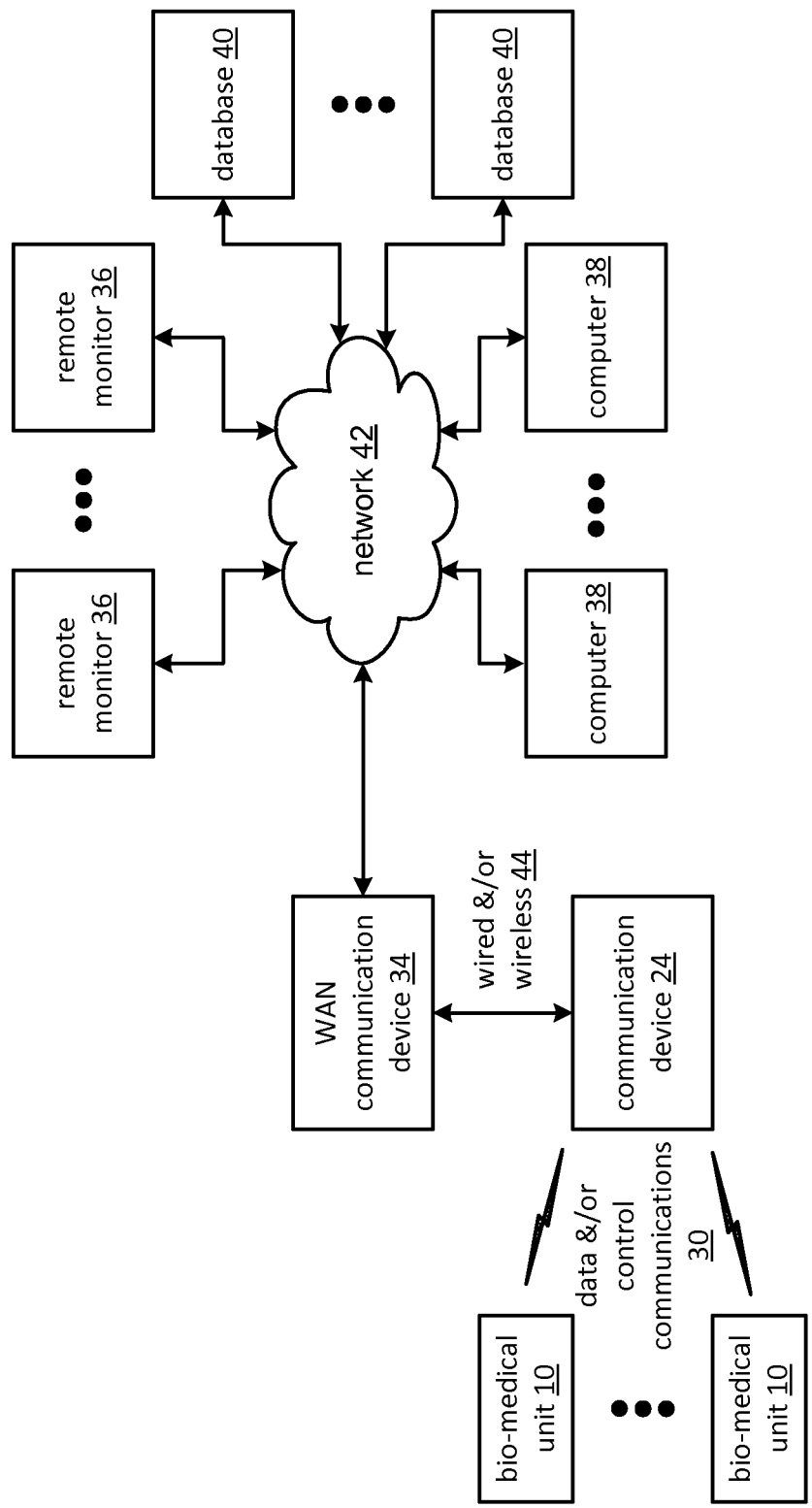
FIG. 5 is a diagram of another embodiment of a system in accordance with the present invention.

FIG. 5 is a diagram of another embodiment of a system that includes a plurality of bio-medical units 10 and one or more communication devices 24 coupled to a wide area network (WAN) communication device 34 (e.g., a cable modem, DSL modem, base station, access point, hot spot, etc.). The WAN communication device 34 is coupled to a network 42 (e.g., cellular telephone network, internet, etc.), which is coupled to it a plurality of remote monitors 36, a plurality of databases 40, and a plurality of computers 38.

In an example of operation, one or more of the remote monitors 36 may receive images and/or other data 30 from one or more of the bio-medical units 10 via the communication device 24, the WAN communication device 34, and the network 42. In this manner, a person(s) operating the remote monitors 36 may view images and/or the data 30 gathered by the bio-medical units 10. This enables a specialist to be consulted without requiring the patient to travel to the specialist's office.

In another example of operation, one or more of the computers 38 may communicate with the bio-medical units 10 via the communication device 24, the WAN communication device 34, and the network 42. In this example, the computer 36 may provide commands 30 to one or more of the bio-medical units 10 to gather data, to dispense a medication, to move to a new position in the body, to perform a mechanical function (e.g., cut, grasp, drill, puncture, stitch, patch, etc.), etc. As such, the bio-medical units 10 may be remotely controlled via one or more of the computers 36.

In another example of operation, one or more of the bio-medical units 10 may read and/or write data from or to one or more of the databases 40. For example, data (e.g., a blood sample analysis) generated by one or more of the bio-medical units 10 may be written to one of the databases 40. The communication device 24 and/or one of the computers 36 may control the writing of data to or the reading of data from the database(s) 40. The data may further include medical records, medical images, prescriptions, etc.

Figure 6:
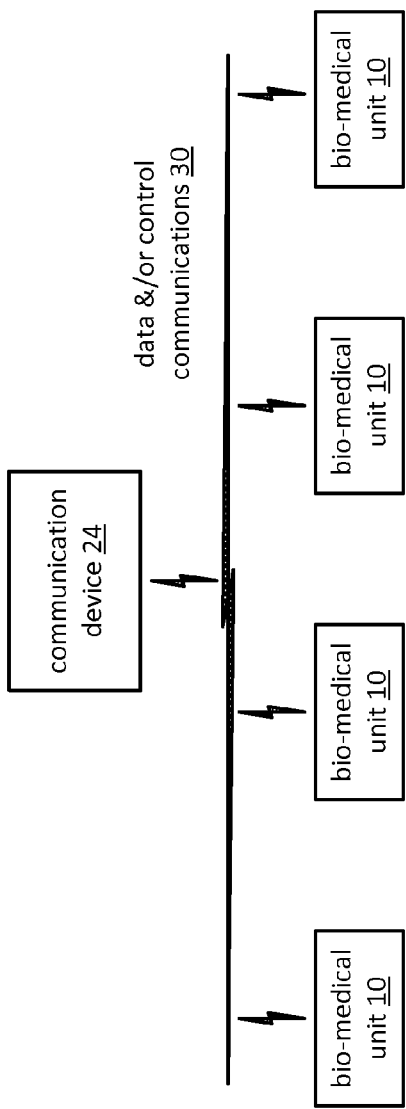
FIG. 6 is a diagram of another embodiment of a system in accordance with the present invention.

FIG. 6 is a diagram of another embodiment of a system that includes a plurality of bio-medical units 10. In this embodiment, the bio-medical units 10 can communicate with each other directly and/or communicate with the communication device 24 directly. The communication medium may be an infrared channel(s), an RF channel(s), a MMW channel(s), and/or ultrasound. The units may use a communication protocol such as token passing, carrier sense, time division multiplexing, code division multiplexing, frequency division multiplexing, etc.

Figure 7:
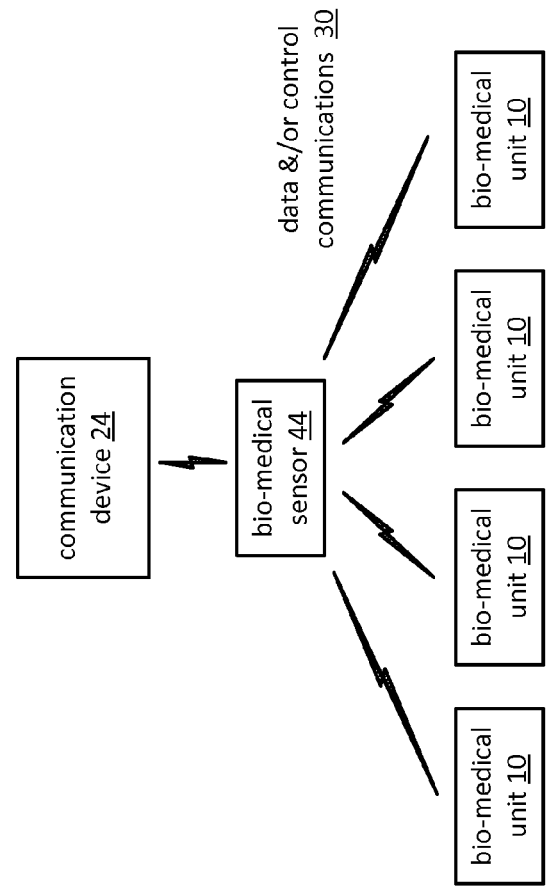
FIG. 7 is a diagram of another embodiment of a system in accordance with the present invention.

FIG. 7 is a diagram of another embodiment of a system that includes a plurality of bio-medical units 10. In this embodiment, one of the bio-medical units 44 functions as an access point for the other units. As such, the designated unit 44 routes communications between the units 10 and between one or more units 10 and the communication device 24. The communication medium may be an infrared channel(s), an RF channel(s), a MMW channel(s), and/or ultrasound. The units 10 may use a communication protocol such as token passing, carrier sense, time division multiplexing, code division multiplexing, frequency division multiplexing, etc.

Figure 8:
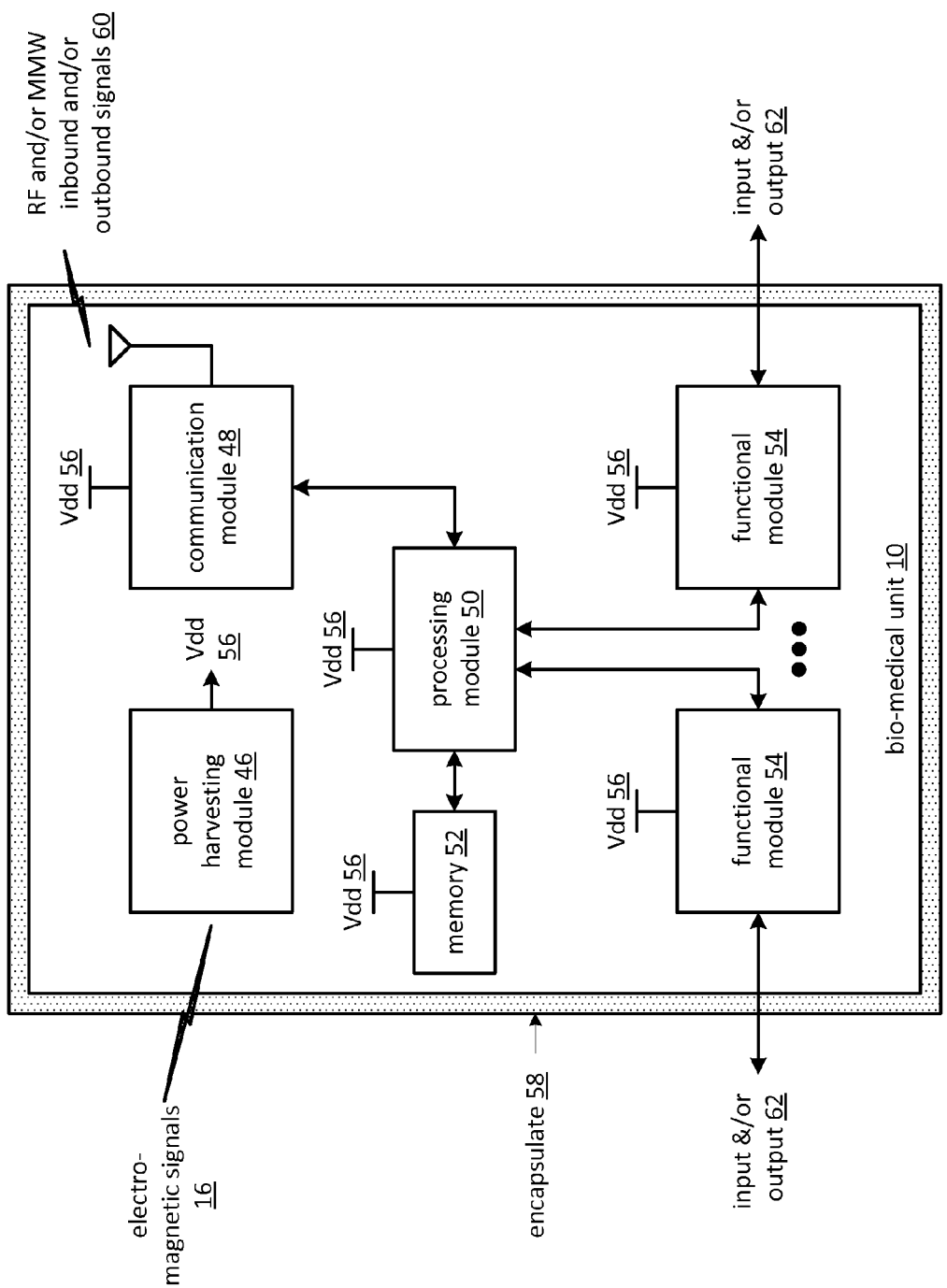
FIG. 8 is a schematic block diagram of an embodiment of a bio-medical unit in accordance with the present invention.

FIG. 8 is a schematic block diagram of an embodiment of a bio-medical unit 10 that includes a power harvesting module 46, a communication module 48, a processing module 50, memory 52, and one or more functional modules 54. The processing module 50 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module 50 may have an associated memory 52 and/or memory element, which may be a single memory device, a plurality of memory devices, and/or embedded circuitry of the processing module. Such a memory device 52 may be a read-only memory, random access memory, volatile memory, non-volatile memory, static memory, dynamic memory, flash memory, cache memory, and/or any device that stores digital information. Note that if the processing module 50 includes more than one processing device, the processing devices may be centrally located (e.g., directly coupled together via a wired and/or wireless bus structure) or may be distributedly located (e.g., cloud computing via indirect coupling via a local area network and/or a wide area network). Further note that when the processing module 50 implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element stores, and the processing module executes, hard coded and/or operational instructions corresponding to at least some of the steps and/or functions illustrated in FIGS. 1-29.

The power harvesting module 46 may generate one or more supply voltages 56 (Vdd) from one or more of MRI electromagnetic signals 16, magnetic fields 26, RF signals, MMW signals, and body motion. The power harvesting module 46 may be implemented as disclosed in U.S. Pat. No. 7,595,732 to generate one or more supply voltages from an RF signal. Alternatively, or in addition to, the power harvesting module 46 may be implemented as shown in one or more FIGS. 9-11 to generate one or more supply voltages 56 from an MRI signal 28 and/or magnetic field 26. As yet another alternative, or a further addition, the power harvesting module 46 may be implemented as shown in FIG. 12 to generate one or more supply voltage 56 from body motion.

The communication module 48 may include a receiver section and a transmitter section. The transmitter section converts an outbound symbol stream into an outbound RF or MMW signal 60 that has a carrier frequency within a given frequency band (e.g., 900 MHz, 2.5 GHz, 5 GHz, 57-66 GHz, etc.). In an embodiment, this may be done by mixing the outbound symbol stream with a local oscillation to produce an up-converted signal. One or more power amplifiers and/or power amplifier drivers amplifies the up-converted signal, which may be RF or MMW bandpass filtered, to produce the outbound RF or MMW signal 60. In another embodiment, the transmitter section includes an oscillator that produces an oscillation. The outbound symbol stream provides phase information (e.g., $+/-\Delta\theta$ [phase shift] and/or $\theta(t)$ [phase modulation]) that adjusts the phase of the oscillation to produce a phase adjusted RF or MMW signal, which is transmitted as the outbound RF signal 60. In another embodiment, the outbound symbol stream includes amplitude information (e.g., $A(t)$ [amplitude modulation]), which is used to adjust the amplitude of the phase adjusted RF or MMW signal to produce the outbound RF or MMW signal 60.

In yet another embodiment, the transmitter section includes an oscillator that produces an oscillation. The outbound symbol provides frequency information (e.g., $+/-\Delta f$ [frequency shift] and/or $f(t)$ [frequency modulation]) that adjusts the frequency of the oscillation to produce a frequency adjusted RF or MMW signal, which is transmitted as the outbound RF or MMW signal 60. In another embodiment, the outbound symbol stream includes amplitude information, which is used to adjust the amplitude of the frequency adjusted RF or MMW signal to produce the outbound RF or MMW signal 60. In a further embodiment, the transmitter section includes an oscillator that produces an oscillation. The outbound symbol provides amplitude information (e.g., $+/-\Delta A$ [amplitude shift] and/or $A(t)$ [amplitude modulation]) that adjusts the amplitude of the oscillation to produce the outbound RF or MMW signal 60.

The receiver section amplifies an inbound RF or MMW signal 60 to produce an amplified inbound RF or MMW signal. The receiver section may then mix in-phase (I) and quadrature (Q) components of the amplified inbound RF or MMW signal with in-phase and quadrature components of a local oscillation to produce a mixed I signal and a mixed Q signal. The mixed I and Q signals are combined to produce an inbound symbol stream. In this embodiment, the inbound symbol may include phase information (e.g., $+/-\Delta\theta$ [phase shift] and/or $\theta(t)$ [phase modulation]) and/or frequency information (e.g., $+/-\Delta f$ [frequency shift] and/or $f(t)$ [frequency modulation]). In another embodiment and/or in furtherance of the preceding embodiment, the inbound RF or MMW signal includes amplitude information (e.g., $+/-\Delta A$ [amplitude shift] and/or $A(t)$ [amplitude modulation]). To recover the amplitude information, the receiver section includes an amplitude detector such as an envelope detector, a low pass filter, etc. Note that, as may be discussed herein, RF may include signals within the radio frequency band of 30 Hz to 3 GHz and/or within the microwave (or MMW) frequency band of 3 GHz to 300 GHz.

The processing module 50 generates the outbound symbol stream from outbound data and converts the inbound symbol stream into inbound data. For example, the processing module 50 converts the inbound symbol stream into inbound data (e.g., voice, text, audio, video, graphics, etc.) in accordance with one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). Such a conversion may include one or more of: digital intermediate frequency to baseband conversion, time to frequency domain conversion, space-time-block decoding, space-frequency-block decoding, demodulation, frequency spread decoding, frequency hopping decoding, beamforming decoding, constellation demapping, deinterleaving, decoding, depuncturing, and/or descrambling.

As another example, the processing module 50 converts outbound data (e.g., voice, text, audio, video, graphics, etc.) into outbound symbol stream in accordance with one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). Such a conversion includes one or more of: scrambling, puncturing, encoding, interleaving, constellation mapping, modulation, frequency spreading, frequency hopping, beamforming, space-time-block encoding, space-frequency-block encoding, frequency to time domain conversion, and/or digital baseband to intermediate frequency conversion.

Each of the one or more functional modules 54 provides a function to support treatment, data gathering, motion, repairs, and/or diagnostics. The functional modules 54 may be implemented using nanotechnology and/or microelectronic mechanical systems (MEMS) technology. Various examples of functional modules 54 are illustrated in one or more of FIGS. 13-29.

The bio-medical unit 10 may be encapsulated by an encapsulate 58 that is non-toxic to the body. For example, the encapsulate 58 may be a silicon based product, a non-ferromagnetic metal alloy (e.g., stainless steel), etc. As another example, the encapsulate 58 may include a spherical shape and have a ferromagnetic liner that shields the unit from a magnetic field and to offset the forces of the magnetic field.

The bio-medical unit 10 may be implemented on a single die that has an area of a few millimeters or less. The die may be fabricated in accordance with CMOS technology, Gallium-Arsenide technology, and/or any other integrated circuit die fabrication process.

Figure 9:
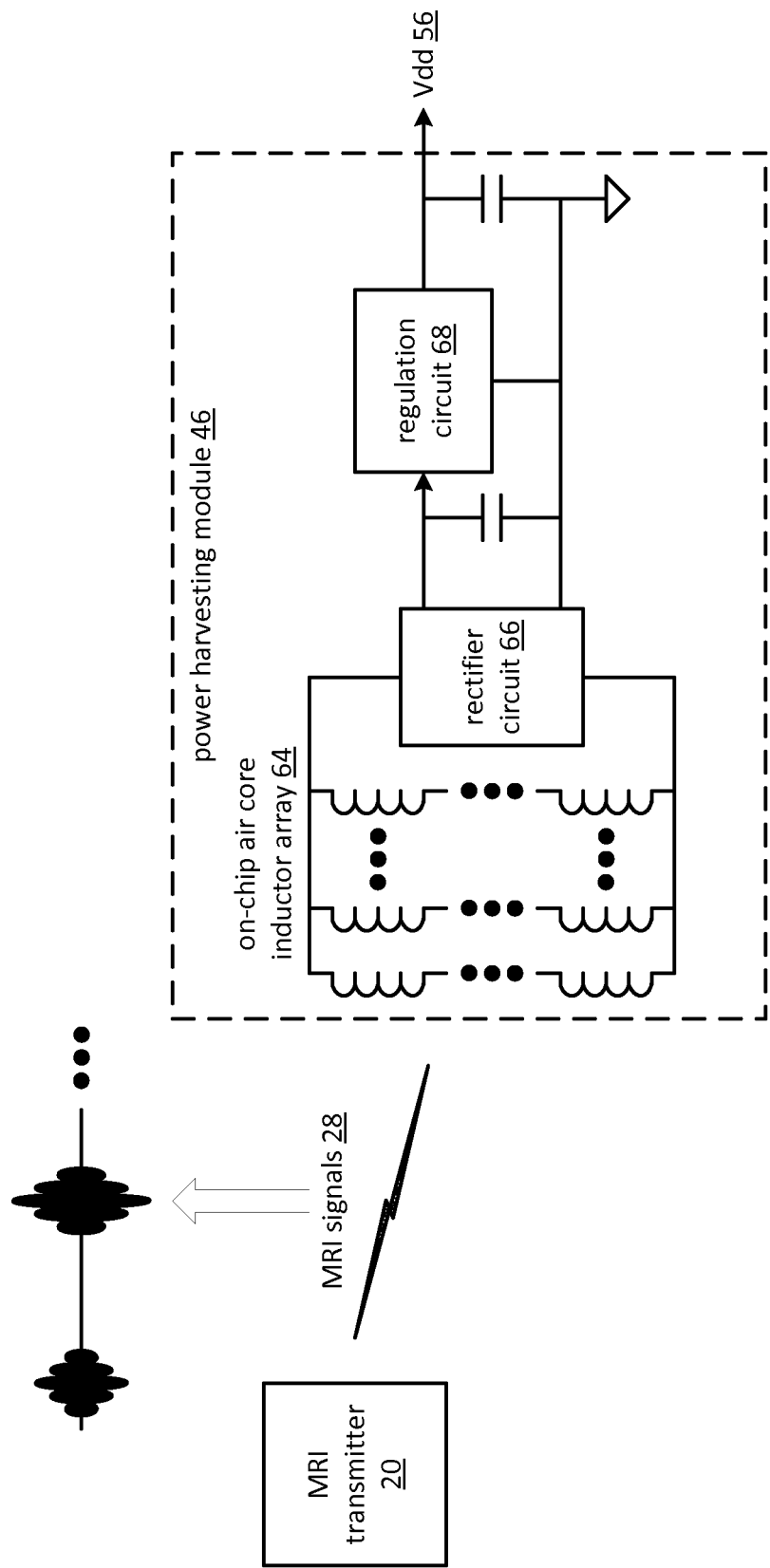
FIG. 9 is a schematic block diagram of an embodiment of a power harvesting module in accordance with the present invention.

FIG. 9 is a schematic block diagram of an embodiment of a power harvesting module 46 that includes an array of on-chip air core inductors 64, a rectifying circuit 66, capacitors, and a regulation circuit 68. The inductors 64 may each have an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 64 are electromagnetically coupled to generate a voltage from the magnetic and/or electric field generated by the MRI signals 28. Alternatively, or in addition to, the air core inductors 64 may generate a voltage from the magnetic field 26 and changes thereof produced by the gradient coils. The rectifying circuit 66 rectifies the AC voltage produced by the inductors to produce a first DC voltage. The regulation circuit generates one or more desired supply voltages 56 from the first DC voltage.

The inductors 64 may be implemented on one more metal layers of the die and include one or more turns per layer. Note that trace thickness, trace length, and other physical properties affect the resulting inductance.

Figure 10:
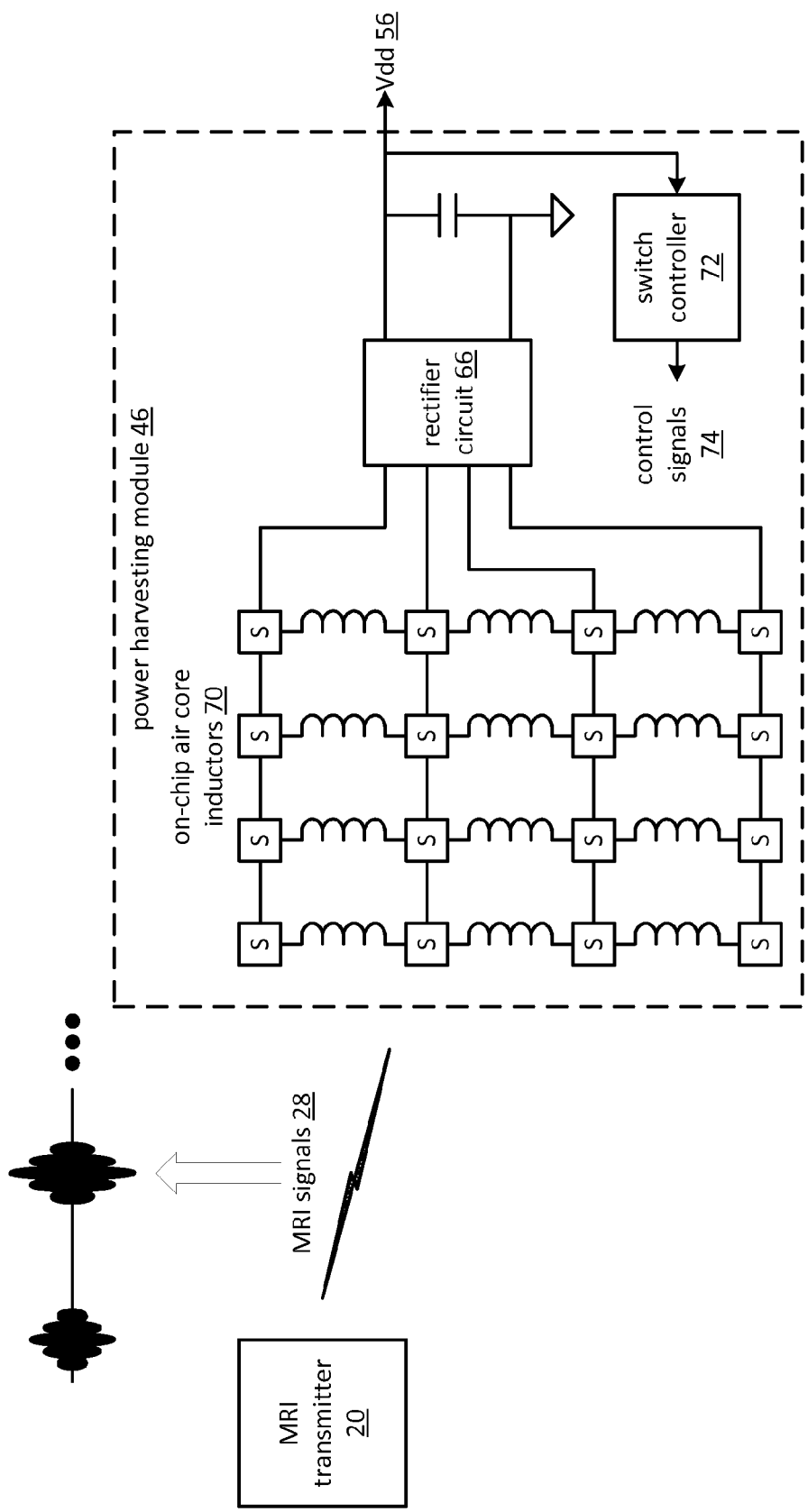
FIG. 10 is a schematic block diagram of another embodiment of a power harvesting module in accordance with the present invention.

FIG. 10 is a schematic block diagram of another embodiment of a power harvesting module 46 that includes a plurality of on-chip air core inductors 70, a plurality of switching units (S), a rectifying circuit 66, a capacitor, and a switch controller 72. The inductors 70 may each having an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 70 are electromagnetically coupled to generate a voltage from the magnetic and/or electric field generated by the MRI signals 28. The switching module 72 engages the switches via control signals 74 to couple the inductors 70 in series and/or parallel to generate a desired AC voltage. The rectifier circuit 66 and the capacitor(s) convert the desired AC voltage into the one or more supply voltages 56.

Figure 11:
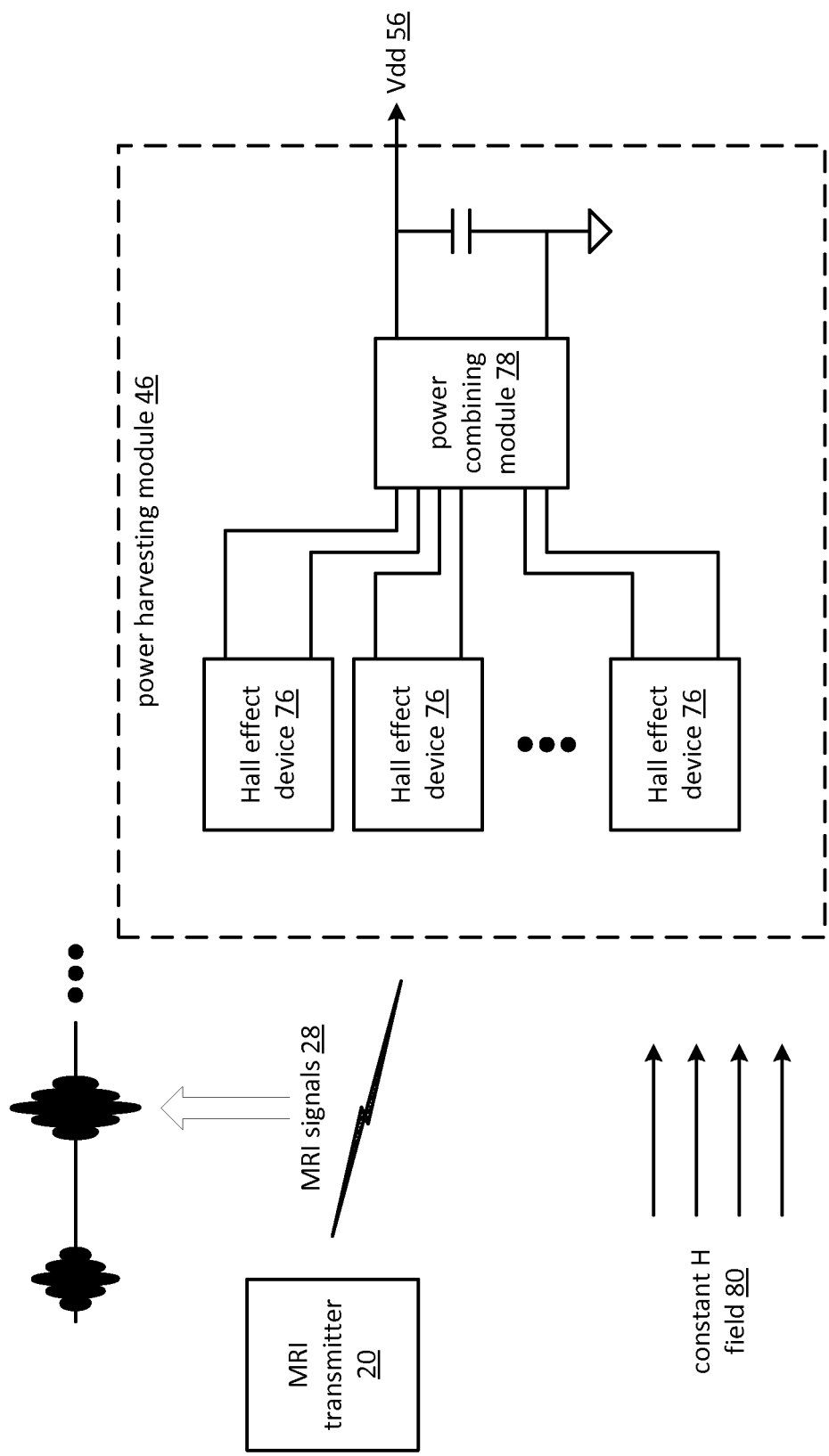
FIG. 11 is a schematic block diagram of another embodiment of a power harvesting module in accordance with the present invention.
Figure 12:
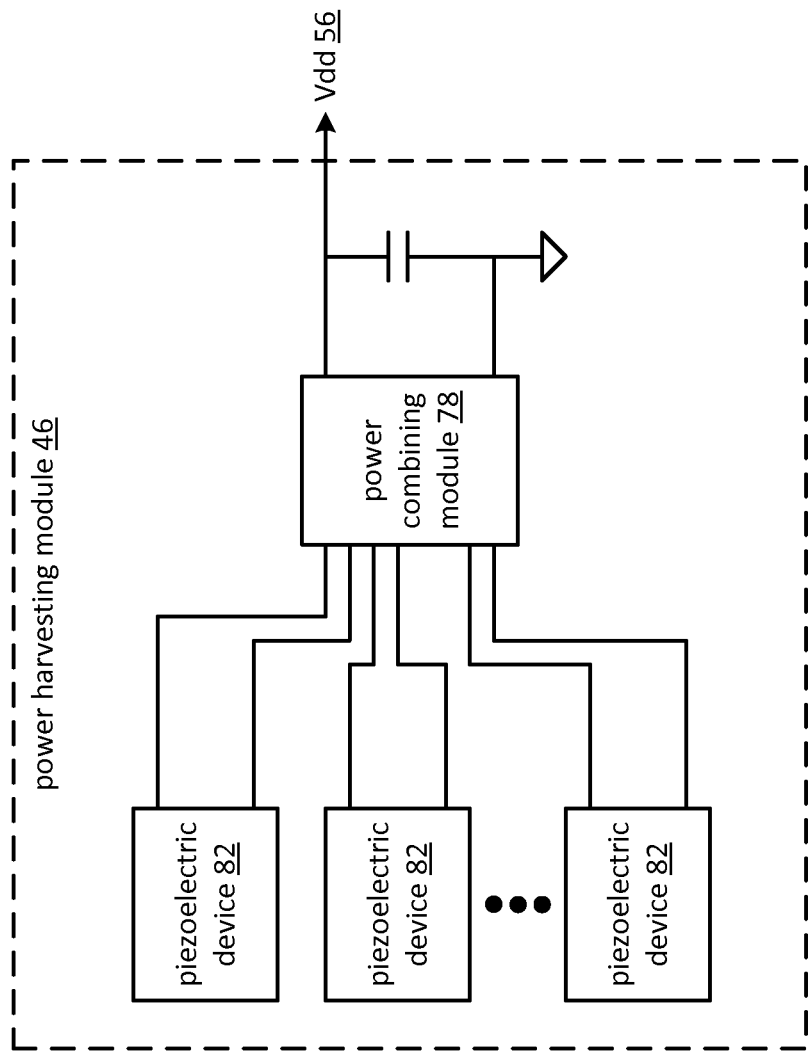
FIG. 12 is a schematic block diagram of another embodiment of a power harvesting module in accordance with the present invention.

FIG. 11 is a schematic block diagram of another embodiment of a power harvesting module 46 that includes a plurality of Hall effect devices 76, a power combining module 78, and a capacitor(s). In an example of operation, the Hall effect devices 76 generate a voltage based on the constant magnetic field (H) and/or a varying magnetic field. The power combining module 78 (e.g., a wire, a switch network, a transistor network, a diode network, etc.) combines the voltages of the Hall effect devices 76 to produce the one or more supply voltages 56.

FIG. 12 is a schematic block diagram of another embodiment of a power harvesting module 46 that includes a plurality of piezoelectric devices 82, a power combining module 78, and a capacitor(s). In an example of operation, the piezoelectric devices 82 generate a voltage based on body movement, ultrasound signals, movement of body fluids, etc. The power combining module 78 (e.g., a wire, a switch network, a transistor network, a diode network, etc.) combines the voltages of the Hall effect devices 82 to produce the one or more supply voltages 56. Note that the piezoelectric devices 82 may include one or more of a piezoelectric motor, a piezoelectric actuator, a piezoelectric sensor, and/or a piezoelectric high voltage device.

The various embodiments of the power harvesting module 46 may be combined to generate more power, more supply voltages, etc. For example, the embodiment of FIG. 9 may be combined with one or more of the embodiments of FIGS. 11 and 12.

Figure 13:
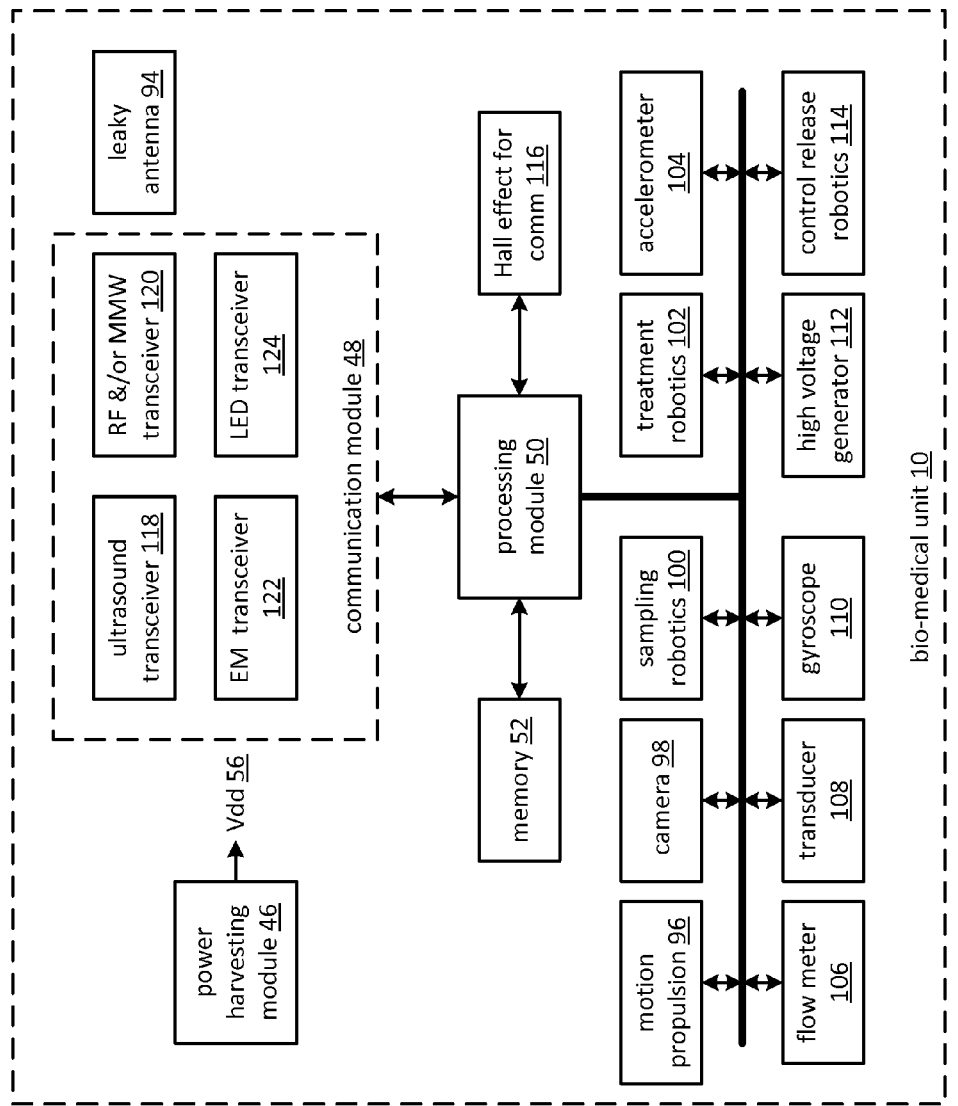
FIG. 13 is a schematic block diagram of another embodiment of a bio-medical unit in accordance with the present invention.

FIG. 13 is a schematic block diagram of another embodiment of a bio-medical unit 10 that includes a power harvesting module 46, a communication module 48, a processing module 50, memory 52, and may include one or more functional modules 54 and/or a Hall effect communication module 116. The communication module 48 may include one or more of an ultrasound transceiver 118, an electromagnetic transceiver 122, an RF and/or MMW transceiver 120, and a light source (LED) transceiver 124. Note that examples of the various types of communication modules 48 will be described in greater detail with reference to one or more of FIGS. 14-29.

The one or more functional modules 54 may perform a repair function, an imaging function, and/or a leakage detection function, which may utilize one or more of a motion propulsion module 96, a camera module 98, a sampling robotics module 100, a treatment robotics module 102, an accelerometer module 104, a flow meter module 106, a transducer module 108, a gyroscope module 110, a high voltage generator module 112, a control release robotics module 114, and/or other functional modules described with reference to one or more other figures. The functional modules 54 may be implemented using MEMS technology and/or nanotechnology. For example, the camera module 98 may be implemented as a digital image sensor in MEMS technology. Example of these various modules will be described in greater detail with reference to one or more of FIGS. 14-29.

The Hall effect communication module 116 utilizes variations in the magnetic field and/or electrical field to produce a plus or minus voltage, which can be encoded to convey information. For example, the charge applied to one or more Hall effect devices 76 may be varied to produce the voltage change. As another example, an MRI transmitter 20 and/or gradient unit may modulate a signal on the magnetic field 26 it generates to produce variations in the magnetic field 26.

Figure 14:
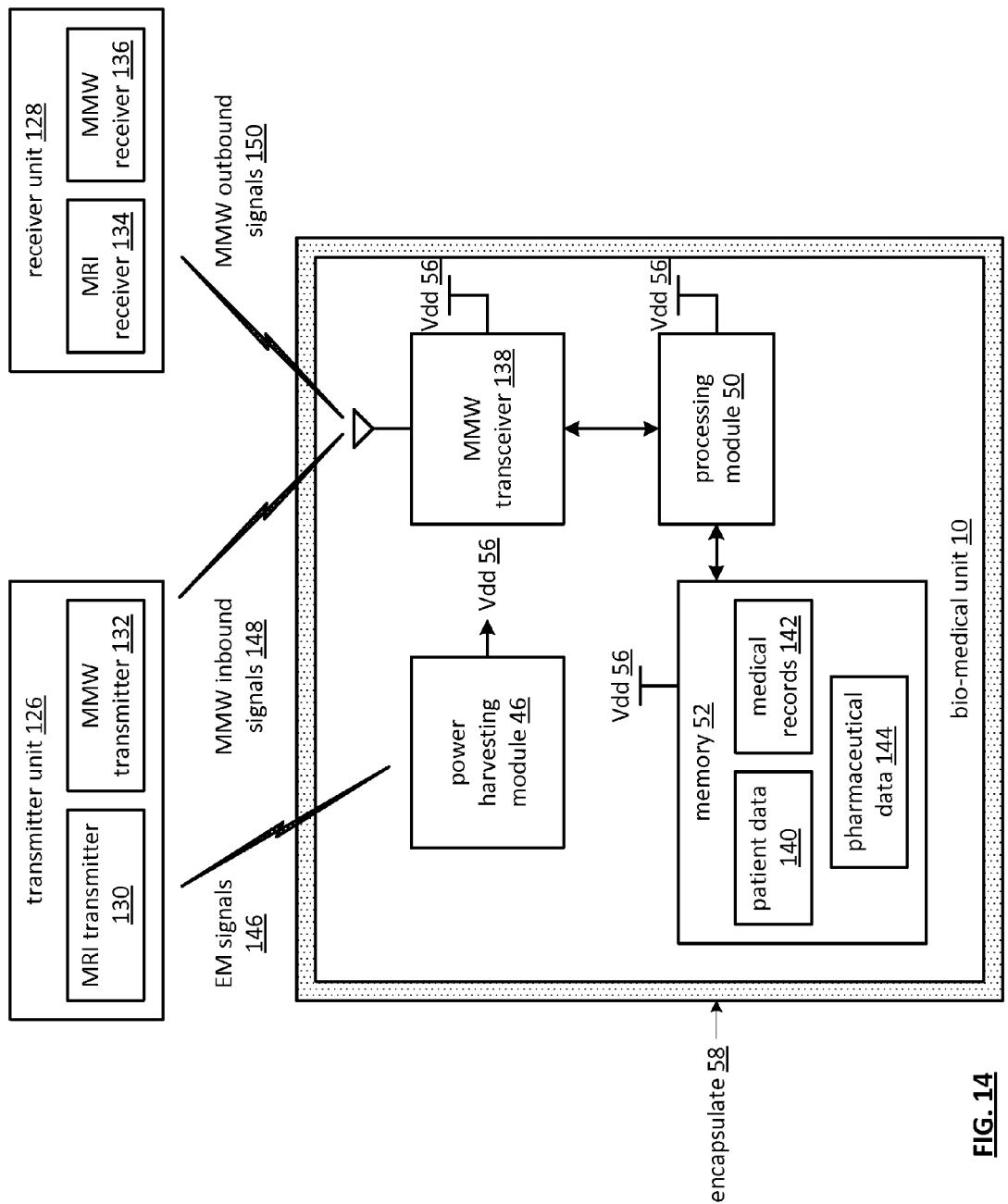
FIG. 14 is a diagram of another embodiment of a system in accordance with the present invention.

FIG. 14 is a diagram of another embodiment of a system that includes one or more bio-medical units 10, a transmitter unit 126, and a receiver unit 128. Each of the bio-medical units 10 includes a power harvesting module 46, an RF and/or MMW (RF) transceiver 138, a processing module 50, memory 52 and one or more functional modules (as shown in one or more of the previous figures). The transmitter unit 126 includes an electromagnetic (e.g., a MRI) transmitter 130 and a MMW transmitter 132. The receiver unit 128 includes an electromagnetic (e.g., MRI) receiver 134 and a MMW receiver 136. Note that the MMW transmitter 132 and MMW receiver 136 may be in the same unit (e.g., in the transmitter unit, in the receiver unit, or housed in a separate device).

Figure 15:
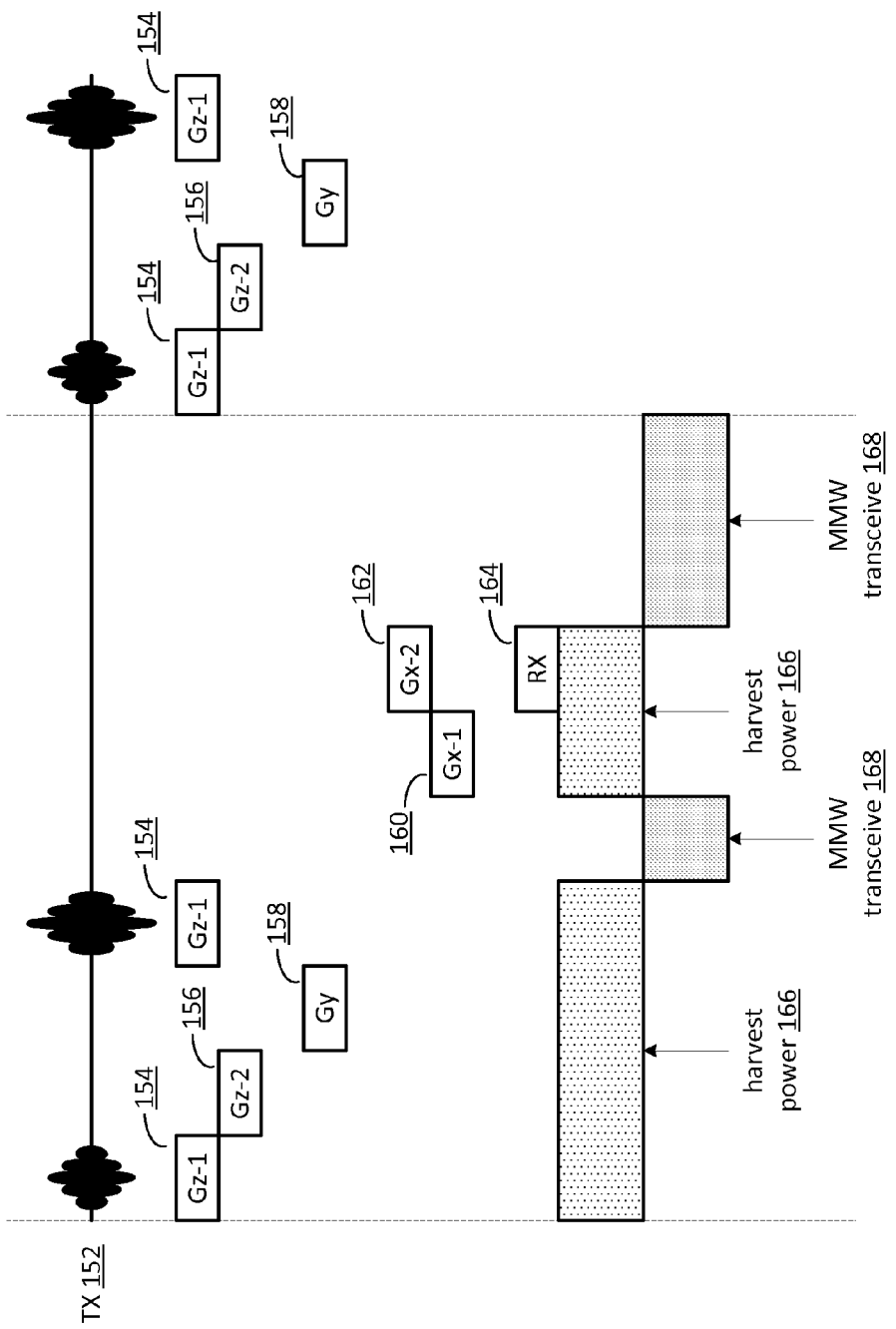
FIG. 15 is a diagram of an example of a communication protocol within a system in accordance with the present invention.

In an example of operation, the electromagnetic transmitter 130 transmits an electromagnetic (EM) signal 146 in a predetermined pattern (e.g., a magnetic resonance imaging (MRI) signal having at least one of a radio frequency (RF) component and a gradient magnetic field component that has a pattern as shown in FIG. 15). In addition, the RF communication transmitter 132 of the transmitter unit 126 transmits a downstream RF communication signal, which may contain a request for data, a command, etc.

The power harvesting module 46 receives the EM signal 146 and generates a power supply voltage therefrom. The RF communication module 138, which is powered by the power supply voltage, receives the downstream RF communication signal during at least one of the null intervals of the transmission pattern. The RF communication module 138 then converts the downstream RF communication signal into downstream information, which includes at least one of downstream data and a downstream instruction.

The functional module performs a bio-medical function based on the at least one of downstream data and the downstream instruction. For example, the bio-medical function may be to take a temperature reading, to release a certain amount of a medication, to take a blood-oxygen reading, etc. As another example, the bio-medical function may cause the bio-medical unit to store the downstream data.

In response to the downstream instruction, or based on another stimulus (e.g., pre-programmed, timed interval, etc.), the bio-medical unit 10 may have data and/or instruction to transmit. In this instance, the function module generates at least one of an upstream instruction and upstream data. The processing module converts the upstream instruction and/or upstream data into upstream information.

The RF communication module 138 interprets the predetermined pattern of the transmitting of the electromagnetic signal to determine null intervals. In addition, the RF communication module 138 converts the upstream information into an upstream RF communication signal and transmits the upstream RF communication signal during one or more of the null intervals. The RF communication receiver 134 of the receiver unit 128 receives the upstream RF communication signal and processes it accordingly.

FIG. 15 is a diagram of an example of a communication protocol within the system of FIG. 14. In this diagram, the MRI transmitter 20 transmits RF signals 152, which have a frequency in the range of 3-45 MHz, at various intervals with varying signal strengths. The power harvesting module 46 of the bio-medical units 10 may use these signals to generate power for the bio-medical unit 10.

In addition to the MRI transmitter 20 transmitting its signal, a constant magnetic field and various gradient magnetic fields 154-164 are created (one or more in the x dimension Gx, one or more in the y dimension Gy, and one or more in the z direction Gz). The power harvesting module 46 of the bio-medical unit 10 may further use the constant magnetic field and/or the varying magnetic fields 154-164 to create power for the bio-medical unit 10.

During non-transmission periods of the cycle, the bio-medical unit 10 may communicate 168 with the MMW transmitter 132 and/or MMW receiver 136. In this regard, the bio-medical unit 10 alternates from generating power to MMW communication in accordance with the conventional transmission-magnetic field pattern of an MRI machine.

Figure 16:
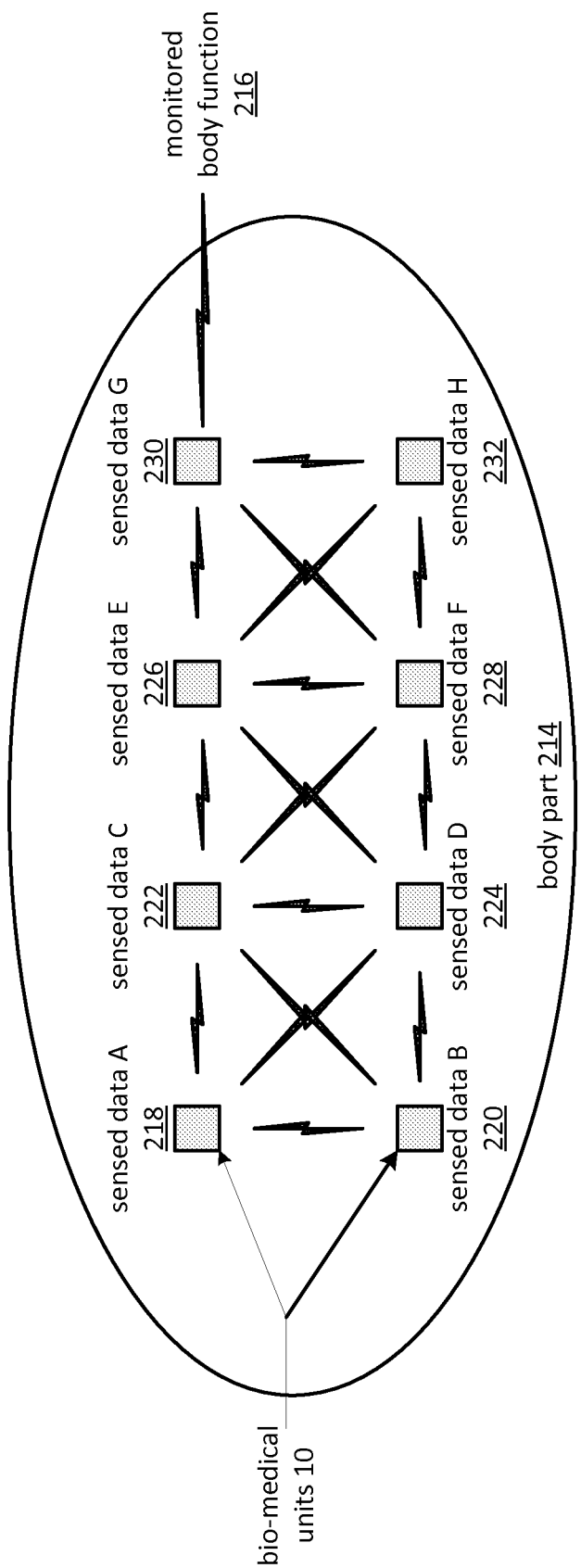
FIG. 16 is a diagram of an embodiment of a network of bio-medical units in accordance with the present invention.

FIG. 16 is a schematic block diagram of an embodiment of networked bio-medical units 10 that communicate with each other, perform sensing functions to produce sensed data 218-232, process the sensed data to produce processed data, and transmit the processed data 216. The bio-medical units 10 may be positioned in a body part to sense data across the body part and to transmit data to an external communication device. The transmitted data may be further processed or aggregated from sensed data.

The bio-medical units 10 may monitor various types of biological functions over a short term or a long term to produce the sensed data 218-232. Note that the sensed data 218-232 may include blood flow rate, blood pressure, temperature, air flow, blood oxygen level, density, white cell count, red cell count, position information, etc.

The bio-medical unit 10 establishes communications with one or more other bio-medical units 10 to facilitate the communication of sensed data 218-232 and processed data 216. The communication may include EM signals, MMW signals, optical signals, sound signals, and/or RF signals.

The bio-medical unit 10 may determine position information based on the sensed data 218-232 and include the position information in the communication. The bio-medical unit 10 may also determine a mode of operation based on one or more of a command, a list, a predetermination, sensed data, and/or processed data. For example, a bio-medical unit 10 at the center of the body part may be in a mode to sense temperature and a bio-medical unit 10 at the outside edge of the body part may sense blood flow.

The bio-medical unit 10 may receive processed data 218-232 from another bio-medical unit and re-send the same processed data 218-232 to yet another bio-medical unit 10. The bio-medical unit 10 may produce processed data based on sensed data 218-232 from the bio-medical unit 10 and/or received processed data from another bio-medical unit 10.

Figure 17:
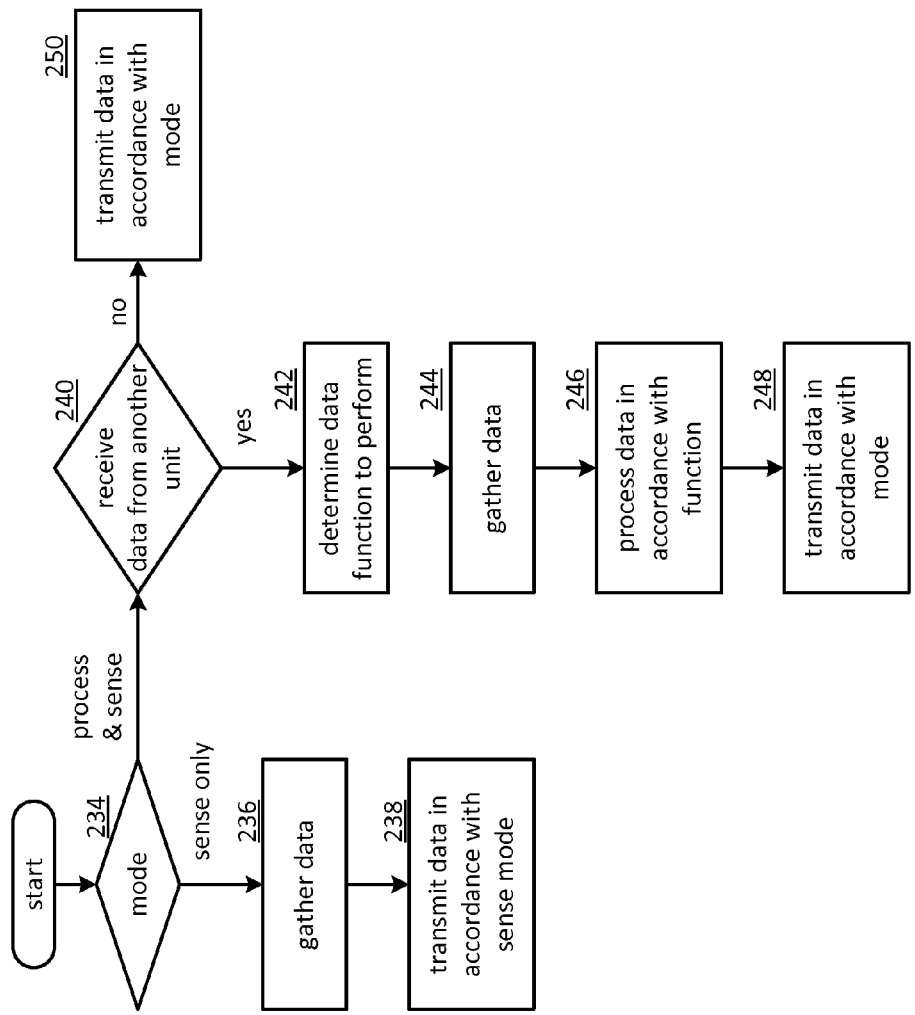
FIG. 17 is a logic diagram of an embodiment of a method for bio-medical unit communications in accordance with the present invention.

FIG. 17 is a flowchart illustrating the processing of networked bio-medical unit data where the bio-medical unit determines the sense mode based on one or more of a predetermination, a stored mode indicator in memory, a command, and/or a dynamic sensed data condition. The method begins at step 234 where the bio-medical unit 10 determines the mode. The method branches to step 240 when the bio-medical unit 10 determines that the mode is process and sense. The method continues to step 236 when the bio-medical unit 10 determines that the mode is sense only.

At step 236, the bio-medical unit 10 gathers data from one or more of the functional modules 54 to produce sensed data. The bio-medical unit 10 may transmit the sensed data 238 to another bio-medical unit 10 and/or an external communication device in accordance with the sense mode. For example, the bio-medical unit 10 may transmit the sensed data at a specific time, to a specific bio-medical unit 10, to a specific external communication device, after a certain time period, when the data is sensed, and/or when the sensed data compares favorably to a threshold (e.g., a temperature trip point).

The method continues at step 240 where the bio-medical unit 10 determines whether it has received data from another unit 10. If not, the method continues to step 250, where the bio-medical unit 10 transmits its sensed data to another bio-medical unit 10 and/or an external communication device in accordance with the sense mode.

When the bio-medical unit 10 has received data from another unit, the method continues at step 242, where the bio-medical unit 10 determines a data function to perform based on one or more of the content of the received data, the sensed data, a command, and/or a predetermination. The data function may one or more of initialization, comparing, compiling, and/or performing a data analysis algorithm.

The method continues at step 244, where the bio-medical unit 10 gathers data from the functional modules 54, and/or the received data from one or more other bio-medical units 10. The method continues at step 246, where the bio-medical unit 10 processes the data in accordance with a function to produce processed data. In addition to the example provided above, the function may also include the functional assignment of the bio-medical unit 10 as determined by a predetermination, a command, sensed data, and/or processed data (e.g., measure blood pressure from the plurality of bio-medical units and summarize the high, low, and average).

The method continues at step 248, where the bio-medical unit 10 transmits the processed data to another bio-medical unit 10 and/or to an external communication device in accordance with the sense mode. For example, the bio-medical unit 10 may transmit the sensed data at a specific time, to a specific bio-medical unit 10, to a specific external communication device, after a certain time period, when the data is sensed, and/or when the sensed data compares favorably to a threshold (e.g., a temperature trip point). Note that the communication protocol may be the same or different between bio-medical units 10 and/or between the bio-medical unit 10 and the external communication device.

Figure 18:
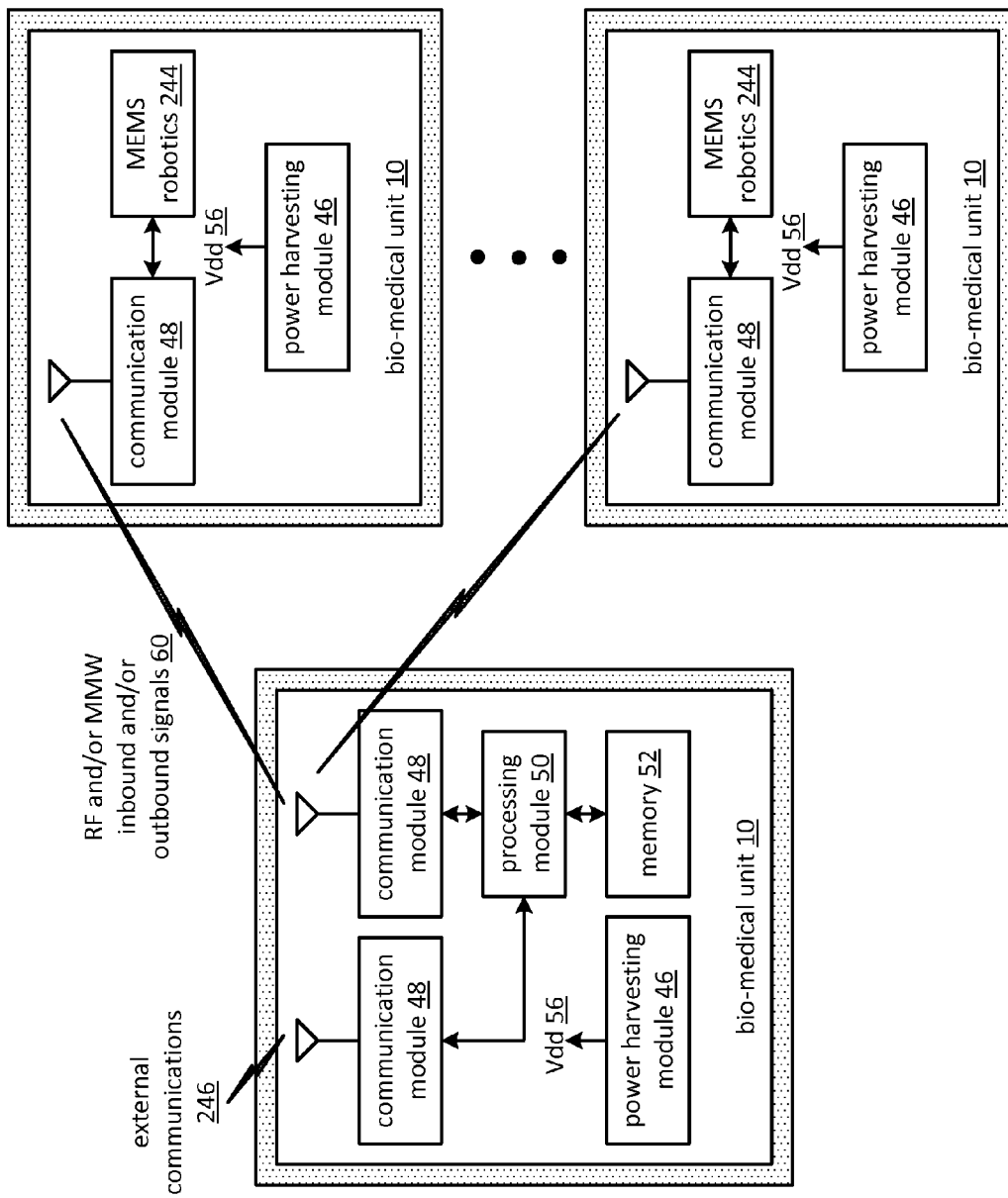
FIG. 18 is a diagram of an embodiment of a network of bio-medical units that include MEMS robotics in accordance with the present invention.

FIG. 18 is a schematic block diagram of an embodiment of a parent bio-medical unit (on the left) communicating with an external unit to coordinates the functions of one or more children bio-medical units 10 (on the right). The parent unit includes a communication module 48 for external communications, a communication module 48 for communication with the children units, the processing module 50, the memory 52, and the power harvesting module 46. Note that the parent unit may be implemented one or more chips and may in the body or one the body.

Each of the child units includes a communication module 48 for communication with the parent unit and/or other children units, a MEMS robotics 244, and the power harvesting module 46. The MEMS robotics 244 may include one or more of a MEMS technology saw, drill, spreader, needle, injection system, and actuator. The communication module 48 may support RF and/or MMW inbound and/or outbound signals 60 to the parent unit such that the parent unit may command the child units in accordance with external communications commands.

In an example of operation, the patent bio-medical unit receives a communication from the external source, where the communication indicates a particular function the child units are to perform. The parent unit processes the communication and relays relative portions to the child units in accordance with a control mode. Each of the child units receives their respective commands and performs the corresponding functions to achieve the desired function.

Figure 19:
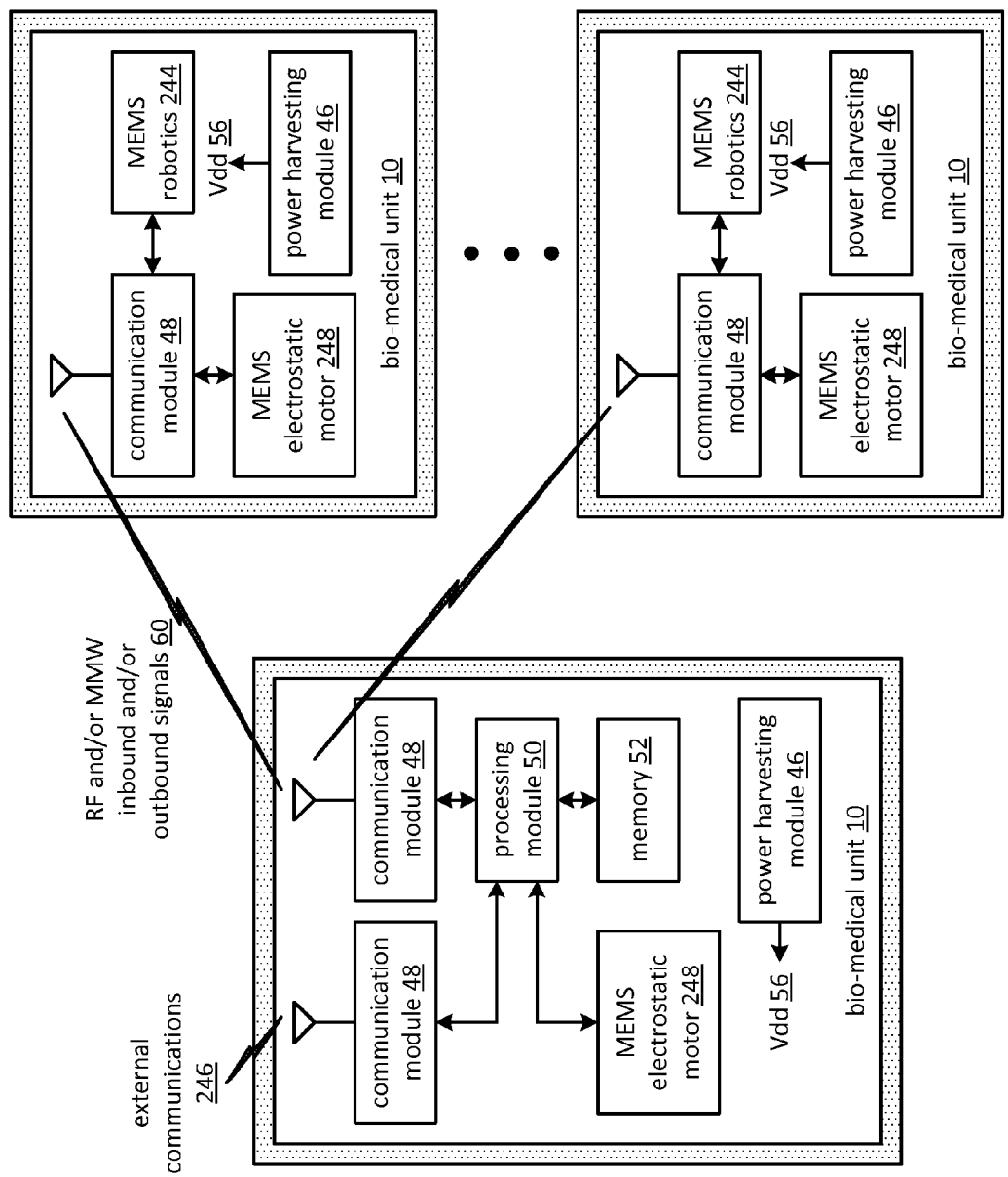
FIG. 19 is a diagram of another embodiment of a network of bio-medical units that include MEMS robotics in accordance with the present invention.

FIG. 19 is a schematic block diagram of another embodiment of a plurality of task coordinated bio-medical units 10 including a parent bio-medical unit 10 (on the left) and one or more children bio-medical units 10 (on the right). The parent unit may be implemented one or more chips and may in the body or one the body. The parent unit may harvest power in conjunction with the power booster 84.

The parent unit includes the communication module 48 for external communications, the communication module 48 for communication with the children units, the processing module 50, the memory 52, a MEMS electrostatic motor 248, and the power harvesting module 46. The child unit includes the communication module 48 for communication with the parent unit and/or other children units, a MEMS electrostatic motor 248, the MEMS robotics 244, and the power harvesting module 46. Note that the child unit has fewer components as compared to the parent unit and may be smaller facilitating more applications where smaller bio-medical units 10 enhances their effectiveness.

The MEMS robotics 244 may include one or more of a MEMS technology saw, drill, spreader, needle, injection system, and actuator. The MEMS electrostatic motor 248 may provide mechanical power for the MEMS robotics 244 and/or may provide movement propulsion for the child unit such that the child unit may be positioned to optimize effectiveness. The child units may operate in unison to affect a common task. For example, the plurality of child units may operate in unison to saw through a tissue area.

The child unit communication module 48 may support RF and/or MMW inbound and/or outbound signals 60 to the parent unit such that the parent unit may command the children units in accordance with external communications commands.

The child unit may determine a control mode and operate in accordance with the control mode. The child unit determines the control mode based on one or more of a command from a parent bio-medical unit, external communications, a preprogrammed list, and/or in response to sensor data. Note that the control mode may include autonomous, parent (bio-medical unit), server, and/or peer as previously discussed.

Figure 20:
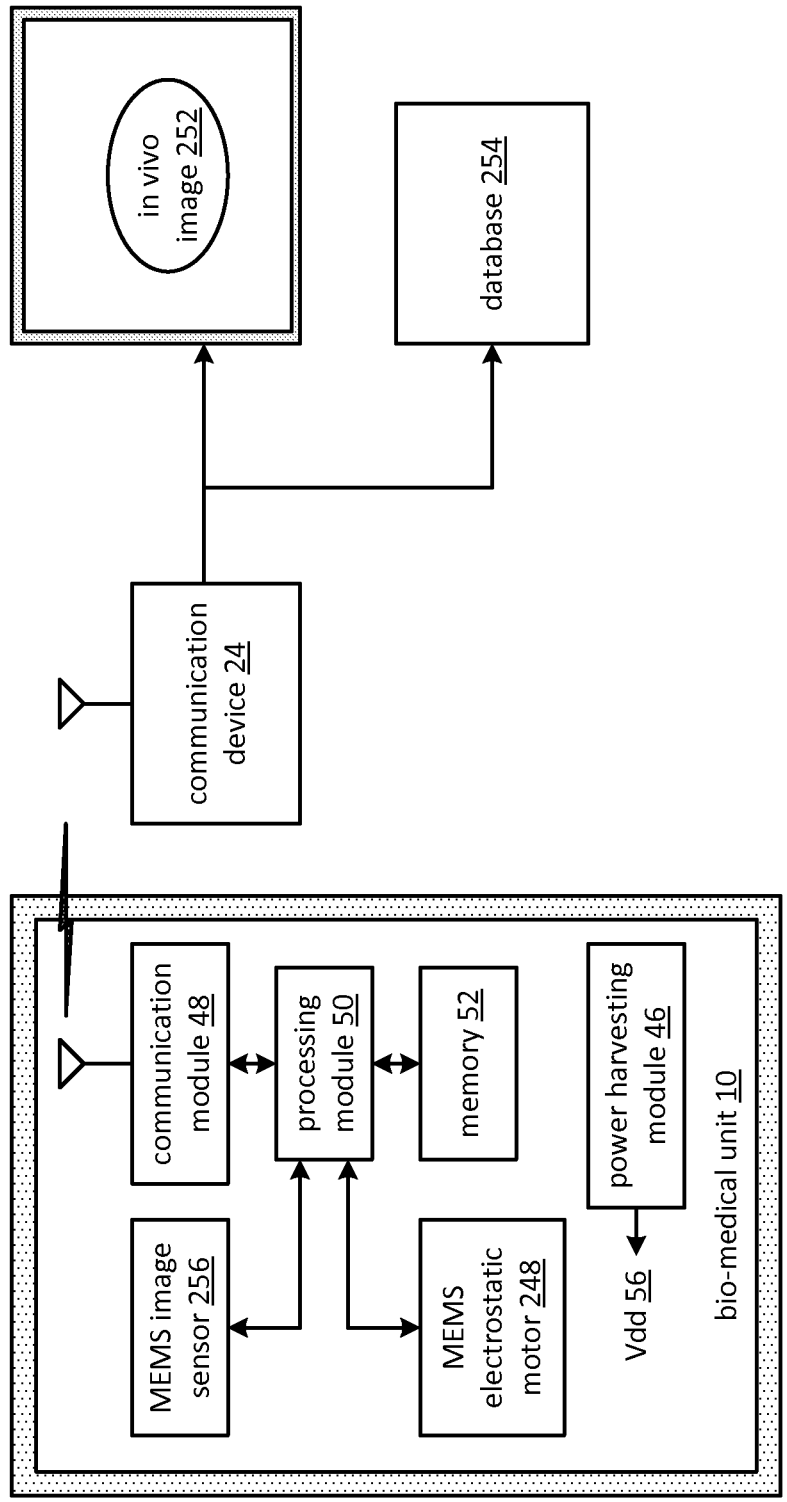
FIG. 20 is a diagram of an embodiment of a bio-medical unit collecting image data in accordance with the present invention.

FIG. 20 is a schematic block diagram of an embodiment of a bio-medical unit 10 based imaging system that includes the bio-medical unit 10, the communication device 24, a database 254, and an in vivo image unit 252. The bio-medical unit 10 may perform scans and provide the in vivo image unit 252 with processed image data for diagnostic visualization.

The bio-medical unit 10 includes a MEMS image sensor 256, the communication module 48 for external communications with the communication device, the processing module 50, the memory 52, the MEMS electrostatic motor 248, and the power harvesting module 46. In an embodiment the bio-medical unit 10 and communication device 24 communicate directly. In another embodiment, the bio-medical unit 10 and communication device 24 communicate through one or more intermediate networks (e.g., wireline, wireless, cellular, local area wireless, Bluetooth, etc.). The MEMS image sensor 256 may include one or more sensors scan types for optical signals, MMW signals, RF signals, EM signals, and/or sound signals.

The in vivo unit 252 may send a command to the bio-medical unit 10 via the communication device 24 to request scan data. The request may include the scan type. The in vivo unit 252 may receive the processed image data from the bio-medical unit 10, compare it to data in the database 254, process the data further, and provide image visualization.

Figure 21:
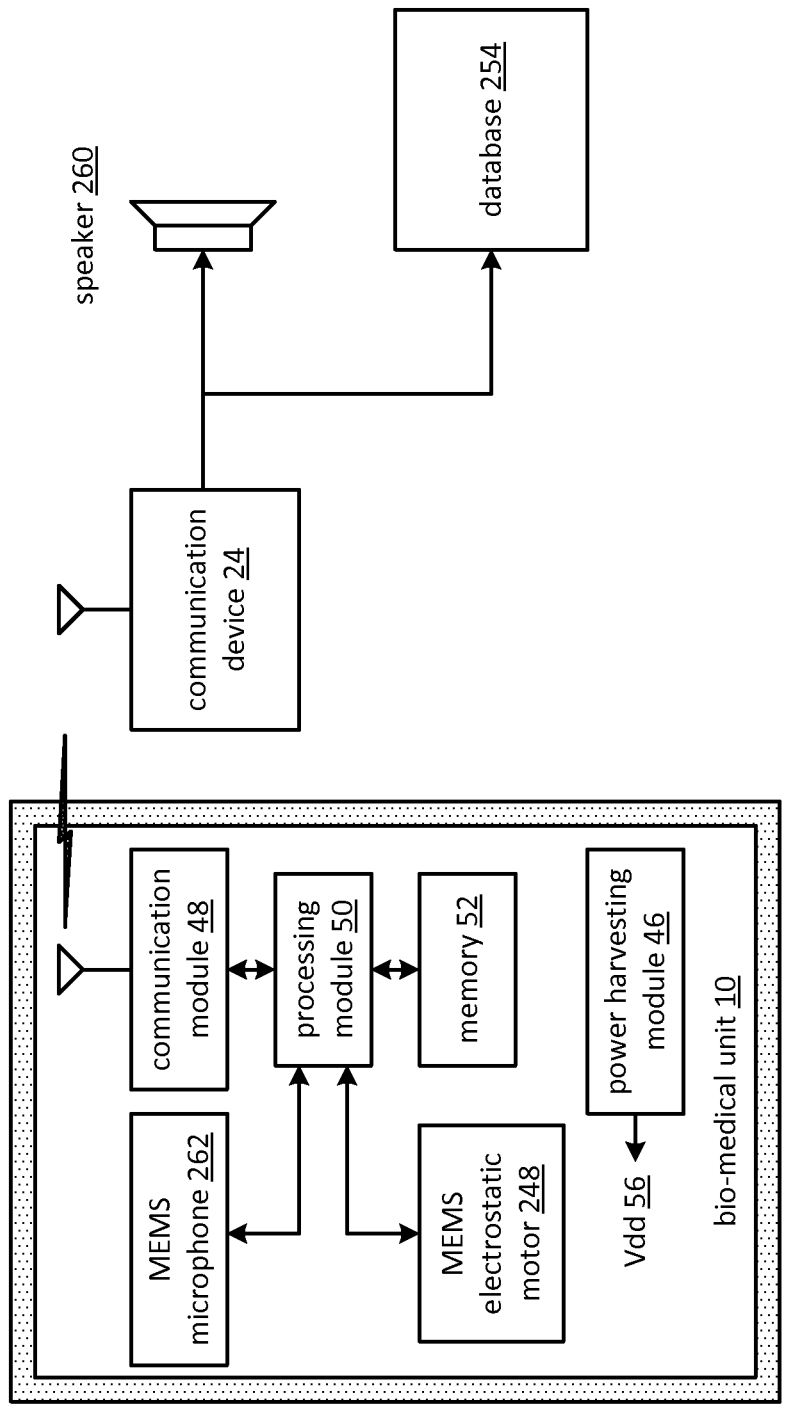
FIG. 21 is a diagram of an embodiment of a bio-medical unit collecting audio and/or ultrasound data in accordance with the present invention.

FIG. 21 is a schematic block diagram of an embodiment of a bio-medical unit 10 based sounding system that includes the bio-medical unit 10, the communication device 24, the database 254, and a speaker 260. The bio-medical unit 10 may perform scans and provide the speaker 260 with processed sounding data for diagnostic purposes via the communication device 24.

The bio-medical unit 10 includes a MEMS microphone 262, the communication module 48 for external communications with the communication device 24, the processing module 50, the memory 52, the MEMS electrostatic motor 248, and the power harvesting module 46. In an embodiment the bio-medical unit 10 and communication device 24 communicate directly. In another embodiment, the bio-medical unit 10 and communication device 24 communicate through one or more intermediate networks (e.g., wireline, wireless, cellular, local area wireless, Bluetooth, etc.) The MEMS microphone 262 may include one or more sensors to detect audible sound signals, sub-sonic sound signals, and/or ultrasonic sound signals.

The processing module 50 may produce the processed sounding data based in part on the received sound signals and in part on data in the database 254. The processing module 50 may retrieve data via the communication module 48 and communication device 24 link from the database 254 to assist in the processing of the signals (e.g., pattern matching, filter recommendations, sound field types). The processing module 50 may process the signals to detect objects, masses, air flow, liquid flow, tissue, distances, etc. The processing module 50 may provide the processed sounding data to the speaker 260 for audible interpretation. In another embodiment, the bio-medical unit 10 assists an ultrasound imaging system by relaying ultrasonic sounds from the MEMS microphone 262 to the ultrasound imaging system instead of to the speaker 260.

Figure 22:
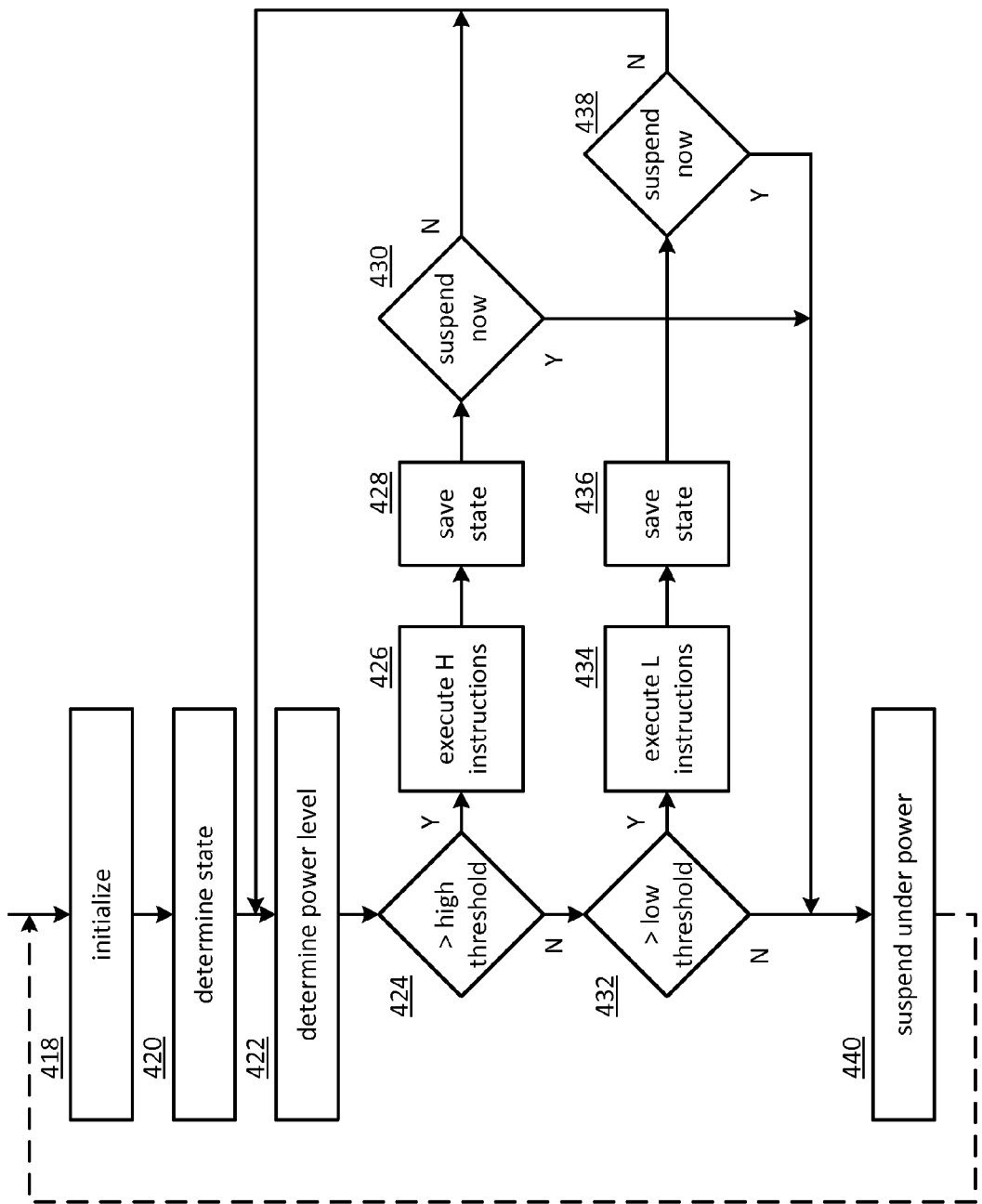
FIG. 22 is a logic diagram of an embodiment of a method for bio-medical unit communications in accordance with the invention.

FIG. 22 is a flowchart of an embodiment of a method for controlling power harvesting within a bio-medical unit 10.

The method begins at step 418 wherein the processing module 50 of the bio-medical unit 10 initializes (e.g., when it is supplied power and wakes up) itself. For example, the processing module 50 executes an initialization boot sequence stored in the memory 52. The initialization boot sequence includes operational instructions that cause the processing module to initialize its registers to accept further instructions. The initialization boot sequence may further include operational instructions to initialize one or more of the communication module 48, the functional module(s) 54 initialized, etc.

The method continues at step 420 where the processing module 50 determines the state of the bio-medical unit (e.g., actively involved in a task, inactive, data gathering, performing a function, etc.). Such a determination may be based on one or more of previous state(s) (e.g., when the processing module was stopped prior to losing power), an input from the functional module 54, a list of steps or elements of a task, the current step of a MRI sequence, and/or new tasks received via the communication module 48.

The method continues at step 422 where the processing module 50 determines the bio-medical unit power level, which may be done by measuring the power harvesting module 46 output Vdd 56. Note that voltage is one proxy for the power level and that other proxies may be utilized including estimation of milliWatt-hours available, a time of operation before loss of operating power estimate, a number of CPU instructions estimate, a number of task elements, a number of tasks estimate, and/or another other estimator to assist in determining how much the bio-medical unit 10 can accomplish prior to losing power. Further note that the processing module 50 may save historic records of power utilization in the memory 52 to assist in subsequent determinations of the power level.

The method continues at step 424 where the processing module 50 compares the power level to the high threshold (e.g., a first available power level that allows for a certain level of processing). If yes, the method continues to step 426 where the processing module 50 enables the execution of H number of instructions. The processing module 50 may utilize a predetermined static value of the H instructions or a dynamic value that changes as a result of the historic records. For example, the historic records may indicate that there was an average of 20% more power capacity left over after the last ten times of instruction execution upon initialization. The processing module 50 may adjust the value of H upward such that the on-going left over power is less than 20% in order to more fully utilize the available power each time the bio-medical unit 10 has power.

The method continues at step 428 where the processing module 50 saves the state in the memory 52 upon completion of the execution of the H instructions such that the processing module 50 can start in a state in accordance with this state upon the next initialization. The method then continues at step 430 where the processing module 50 determines whether it will suspend operations based on one or more of a re-determined power level (e.g., power left after executing the instructions), a predetermined list, a task priority, a task state, a priority indicator, a command, a message, and/or a functional module input. If not, the method repeats at step 422. If yes, the method branches to step 440 where the processing module 50 suspends operations of the bio-medical unit.

If, at step 424, the power level is not greater than the high threshold, the method continues at step 432 where the processing module 50 determines whether the power level compares favorably to a low threshold. If not, the method continues a step 440 where the processing module 50 suspends operations of the bio-medical unit.

If the comparison at step 432 was favorable, the method continues at step 434 where the processing module 50 executes L instructions. The processing module 50 may utilize a predetermined static value of the L instructions or a dynamic value that changes as a result of the historic records as discussed previously. For example, the historic records may indicate that there was an average of 10% more power capacity left over after the last ten times of instruction execution upon initialization. The processing module 50 may adjust the value of L downward such that the on-going left over power is less than 10% in order to more fully utilize the available power each time the bio-medical unit 10 has power.

The method continues at step 436 where the processing module 50 saves the state in the memory 52 upon completion of the execution of the L instructions such that the processing module 50 can start in a state in accordance with this state upon the next initialization. The method then continues at step 438 where the processing module 50 determines whether it will suspend operations based on one or more of a re-determined power level (e.g., power left after executing the instructions), a predetermined list, a task priority, a task state, a priority indicator, a command, a message, and/or a functional module input. If yes, the method branches to step 440. If not, the method repeats at step 422.

Figure 23:
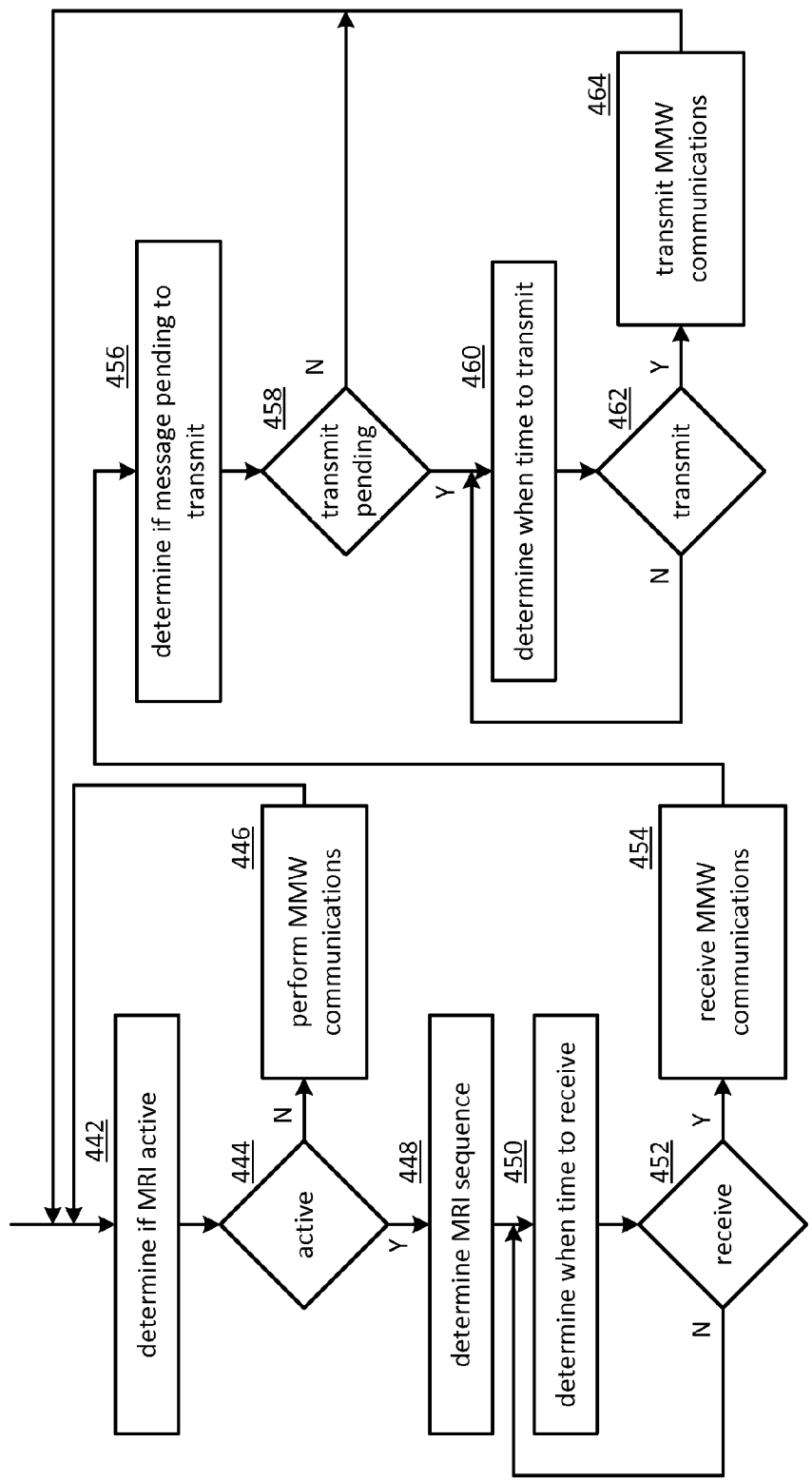
FIG. 23 is a logic diagram of an embodiment of a method for MMW communications within a MRI sequence in accordance with the invention.

FIG. 23 is a flowchart illustrating MMW communications within a MRI sequence where the processing module 50 determines MMW communications in accordance with an MRI sequence. The method begins at step 442 where the processing module 50 determines whether the MRI is active based on receiving MRI EM signals. At step 444, the method branches to step 446 or step 448. When the MRI is active, the method continues at step 446 where the processing module 50 performs MMW communications as previously discussed.

The method continues at step 448 where the processing module 50 determines the MRI sequence based on received MRI EM signals (e.g., gradient pulses and/or MRI RF pulses as shown in one or more of the preceding figures). The method continues at step 450 where the processing module 50 determines whether it is time to perform receive MMW communication in accordance with the MRI sequence. For example, the MMW transceiver 138 may receive MMW inbound signals 148 between any of the MRI sequence steps. As another example, the MMW transceiver 138 may receive MMW inbound signals 148 between specific predetermined steps of the MRI sequence.

At step 452 the method branches back to step 450 or to step 454. When it is time to receive, the method continues at step 454 where the processing module 50 coordinates the MMW transceiver 138 receiving the MMW inbound signals, which may include one or more of a status request, a records request, a sensor data request, a processed data request, a position request, a command, and/or a request for MRI echo signal data. The method then continues at step 456 where the processing module 50 determines whether there is at least one message pending to transmit (e.g., in a transmit queue). At step 458 the method branches back to step 442 or to step 460.

At step 460, the processing module 50 determines when it is time to transmit a MMW communication in accordance with the MRI sequence. For example, the MMW transceiver 138 may transmit MMW outbound signals 150 between any of the MRI sequence steps. As another example, the MMW transceiver 138 may transmit MMW outbound signals 150 between specific predetermined steps of the MRI sequence.

At step 462, the method branches to back step 456 or to step 464. The method continues at step 464 where the processing module 50 coordinates the MMW transceiver 138 transmitting the MMW outbound signals 150, which may include one or more of a status request response, a records request response, a sensor data request response, a processed data request response, a position request response, a command response, and/or a request for MRI echo signal data response. The method then branches back to step 442.

Figure 24:
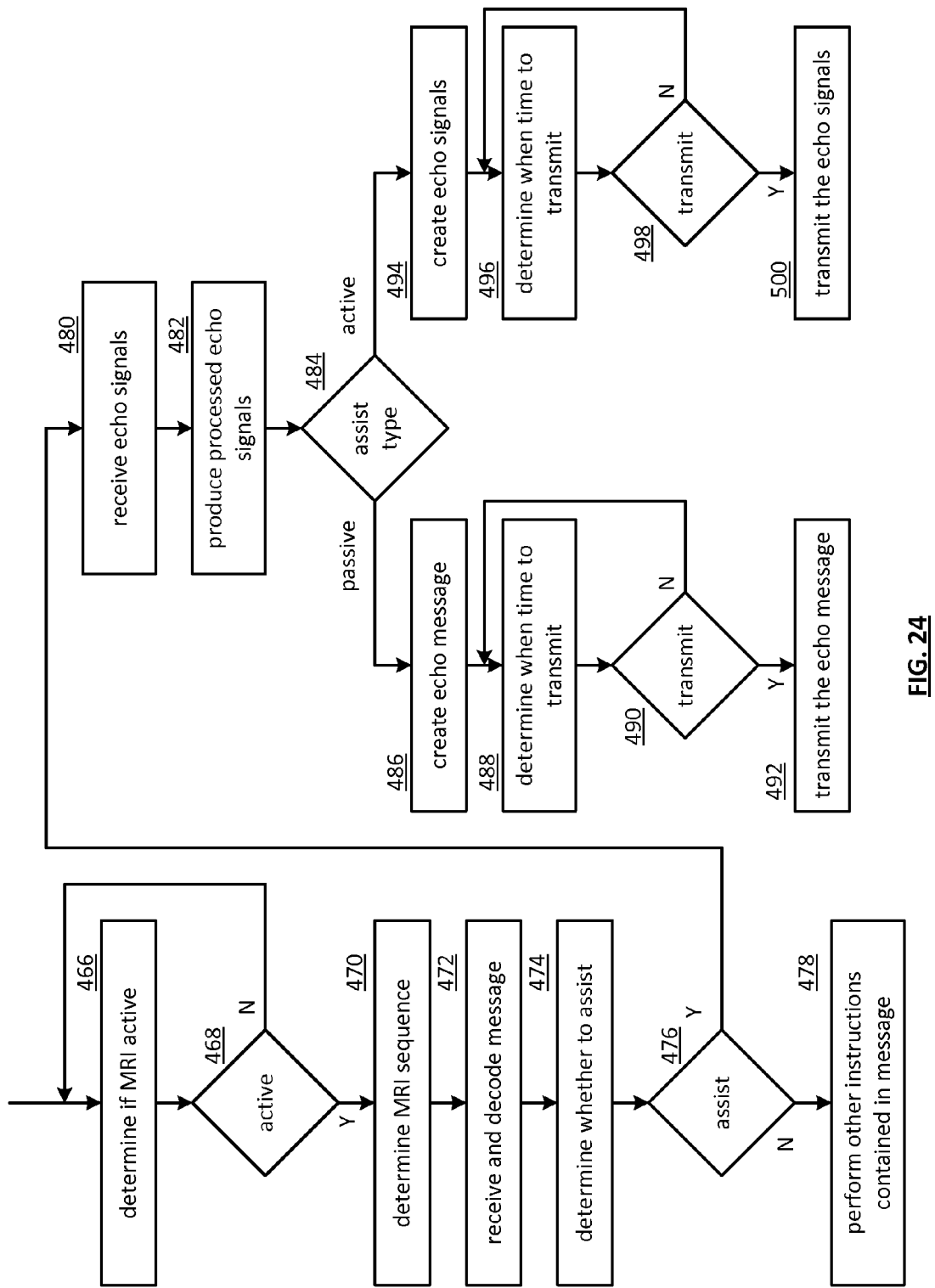
FIG. 24 is a logic diagram of an embodiment of a method for processing of MRI signals in accordance with the present invention.

FIG. 24 is a flowchart illustrating the processing of MRI signals where the processing module 50 of the bio-medical unit 10 may assist the MRI in the reception and processing of MRI EM signals 146. The method begins at step 466 where the processing module 50 determines if the MRI is active based on receiving MRI EM signals 146. The method branches back to step 466 when the processing module 50 determines that the MRI is not active. For example, the MRI sequence may not start until the processing module 50 communicates to the MRI unit that it is available to assist. The method continues to step 470 when the processing module 50 determines that the MRI is active.

At step 470, the processing module 50 determines the MRI sequence based on received MRI EM signals 146 (e.g., gradient pulses and/or MRI RF pulses). At step 472, the processing module receives EM signals 146 and/or MMW communication 532 in accordance with the MRI sequence and decodes a message. For example, the MMW transceiver 138 may receive MMW inbound signals 148 between any of the MRI sequence steps. As another example, the MMW transceiver 138 may receive MMW inbound signals 148 between specific predetermined steps of the MRI sequence. In yet another example, the processing module 50 may receive EM signals 146 at any point of the MRI sequence such that the EM signals 146 contain a message for the processing module 50.

At step 474, the processing module 50 determines whether to assist in the MRI sequence based in part on the decoded message. The determination may be based on a comparison of the assist request to the capabilities of the bio-medical unit 10. At step 476, the method branches to step 480 when the processing module 50 determines to assist in the MRI sequence. The method continues at step 478 where the processing module 50 performs other instructions contained in the message and the method ends.

At step 480, the processing module 50 begins the assist steps by receiving echo signals 530 during the MRI sequence. Note the echo signals 530 may comprise EM RF signals across a wide frequency band as reflected off of tissue during the MRI sequence. At step 482, the processing module 50 processes the received echo signals 530 to produce processed echo signals. Note that this may be a portion of the overall processing required to lead to the desired MRI imaging.

At step 484, the processing module 50 determines the assist type based on the decoded message from the MRI unit. The assist type may be at least passive or active where the passive type collects echo signal 530 information and sends it to the MRI unit via MMW outbound signals 150 and the active type collects echo signal information and re-generates a form of the echo signals 530 and sends the re-generated echo signals to the MRI unit via outbound modulated EM signals (e.g., the MRI unit interprets the re-generated echo signals as echo signals to improve the overall system gain and sensitivity).

The method branches to step 494 when the processing module 50 determines the assist type to be active. The method continues to step 486 when the processing module 50 determines the assist type to be passive. At step 486, the processing module 50 creates an echo message based on the processed echo signals where the echo message contains information about the echo signals 530.

At step 488, the processing module 50 determines when it is time to transmit the echo message encoded as MMW outbound signals 150 via MMW communication in accordance with the MRI sequence. For example, the MMW transceiver 138 may transmit MMW outbound signals 150 between any of the MRI sequence steps. In another example, the MMW transceiver 138 may transmit MMW outbound signals 150 between specific predetermined steps of the MRI sequence.

At step 490, the method branches back to step 488 when the processing module 50 determines that it is not time to transmit the echo message. At step 490, the method continues to step 492 where the processing module 50 transmits the echo message encoded as MMW outbound signals 150.

At step 494, the processing module 50 creates echo signals based on the processed echo signals. At step 496, the processing module 50 determines when it is time to transmit the echo signals as outbound modulated EM signals 180 in accordance with the MRI sequence. At step 498, the method branches back to step 496 when the processing module 50 determines that it is not time to transmit the echo signals. At step 498, the method continues to step 500 where the processing module 50 transmits the echo signals encoded as outbound modulated EM signals 180. Note that the transmitted echo signals emulate the received echo signals 530 with improvements to overcome low MRI power levels and/or low MRI receiver sensitivity.

Figure 25:
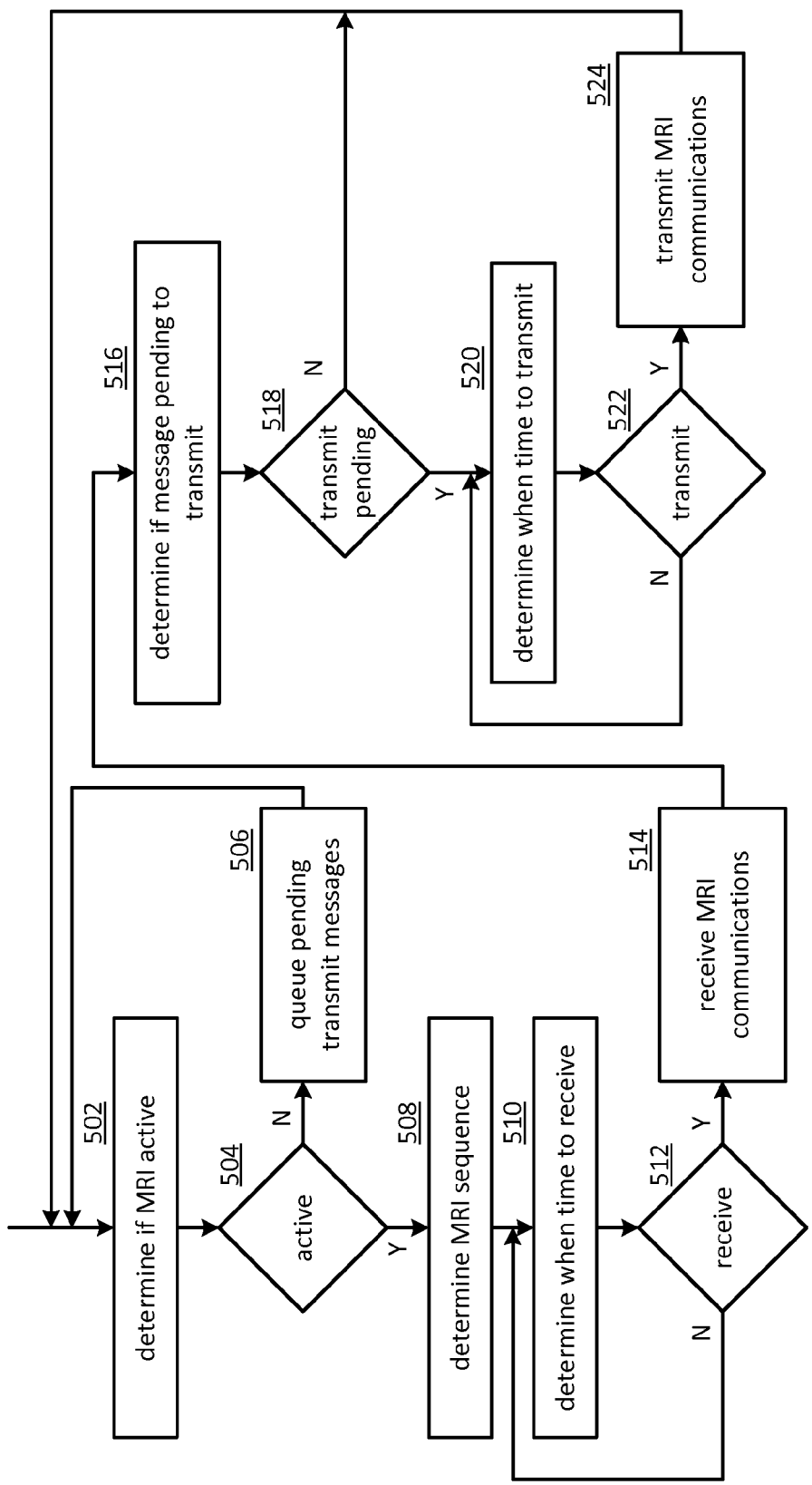
FIG. 25 is a logic diagram of an embodiment of a method for communication utilizing MRI signals in accordance with the present invention.

FIG. 25 is a flowchart illustrating communication utilizing MRI signals where the processing module 50 determines MMW signaling in accordance with an MRI sequence. The method begins at step 502 where the processing module 50 determines if the MRI is active based on receiving MRI EM signals 146. At step 504, the method branches to step 508 when the processing module 50 determines that the MRI is active. At step 504, the method continues to step 506 when the processing module 50 determines that the MRI is not active. At step 506, the processing module 50 queues pending transmit messages. The method branches to step 502.

At step 508, the processing module 50 determines the MRI sequence based on received MRI EM signals 146 (e.g., gradient pulses and/or MRI RF pulses). At step 510, the processing module 50 determines when it is time to perform receive communication in accordance with the MRI sequence. For example, the EM transceiver 174 may receive inbound modulated EM signals 146 containing message information from any of the MRI sequence steps.

At step 512, the method branches back to step 510 when the processing module 50 determines that it is not time to perform receive communication. At step 512, the method continues to step 514 where the processing module 50 directs the EM transceiver 174 to receive the inbound modulated EM signals. The processing module 50 may decode messages from the inbound modulated EM signals 146 such that the messages include one or more of a echo signal collection assist request, a status request, a records request, a sensor data request, a processed data request, a position request, a command, and/or a request for MRI echo signal data. Note that the message may be decoded from the inbound modulated EM signals 146 in one or more ways including detection of the ordering of the magnetic gradient pulses, counting the number of gradient pulses, the slice pulse orderings, detecting small differences in the timing of the pulses, and/or demodulation of the MRI RF pulse.

At step 516 the processing module 50 determines if there is at least one message pending to transmit (e.g., in a transmit queue). At step 518, the method branches back to step 502 when the processing module 50 determines that there is not at least one message pending to transmit. At step 518, the method continues to step 520 where the processing module 50 determines when it is time to perform transmit communication in accordance with the MRI sequence. For example, the EM transceiver 174 may transmit outbound modulated EM signals 180 between any of the MRI sequence steps. In another example, the EM transceiver 174 may transmit the outbound modulated EM signals 180 between specific predetermined steps of the MRI sequence. In yet another example, the EM transceiver 174 may transmit the outbound modulated EM signals 180 in parallel with specific predetermined steps of the MRI sequence, but may utilize a different set of frequencies unique to the EM transceiver 174.

At step 522, the method branches back to step 520 when the processing module 50 determines that it is not time to perform transmit communication. At step 522, the method continues to step 524 where the processing module 50 directs the EM transceiver 174 to prepare the outbound modulated EM signals 180 based on the at least one message pending to transmit. The processing module 50 may encode messages into the outbound modulated EM signals 180 such that the messages include one or more of a status request response, a records request response, a sensor data request response, a processed data request response, a position request response, a command response, and/or a request for MRI echo signal data response. The method branches back to step 502.

Figure 26:
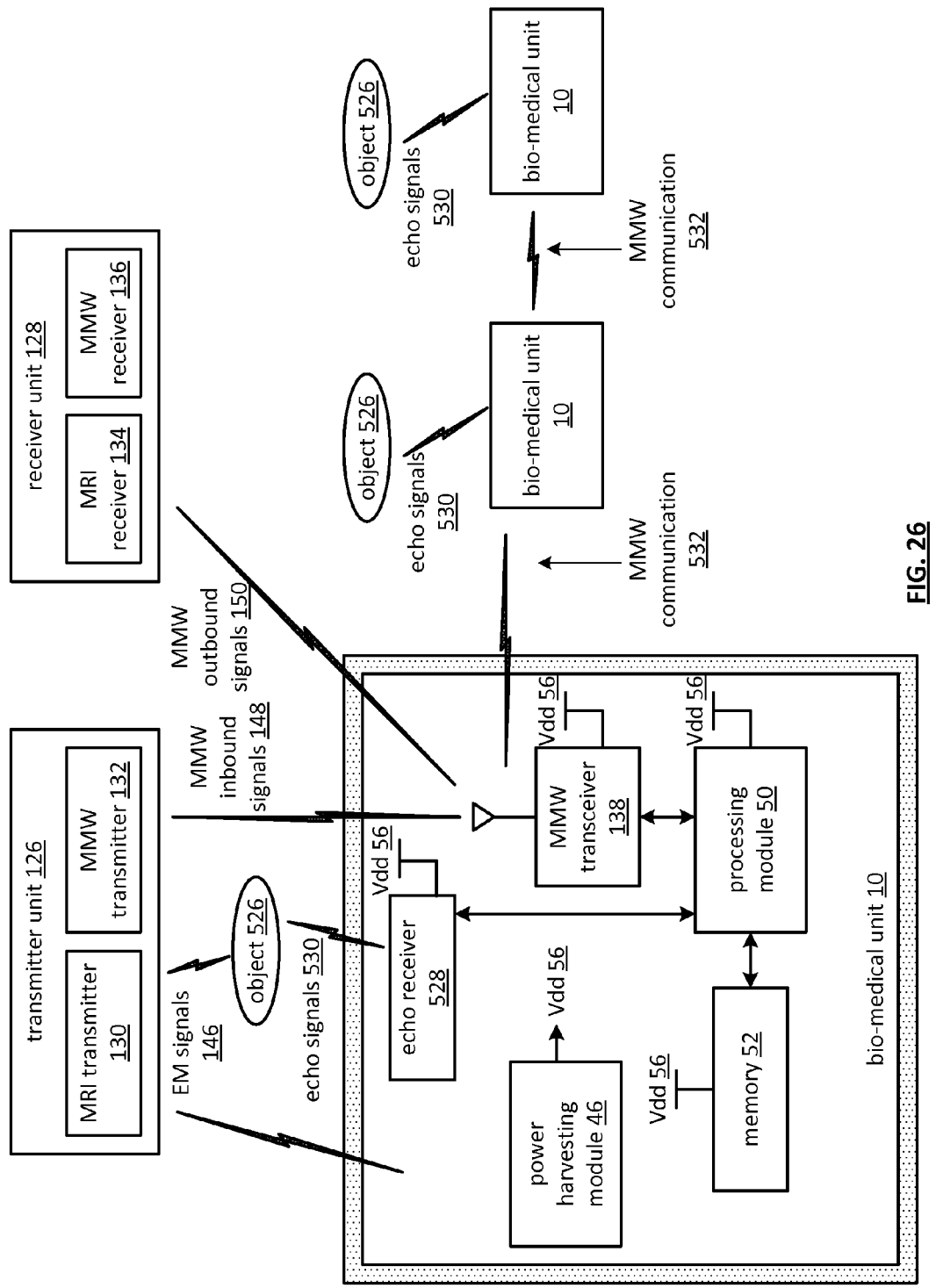
FIG. 26 is a schematic block diagram of another embodiment of a bio-medical unit in accordance with the present invention.

FIG. 26 is a schematic block diagram of an embodiment of a MRI system utilizing a plurality of bio-medical units 10 to provide processed echo signal information based on received MRI echo signals 530 across the plurality of bio-medical units 10. The MRI system includes the transmitter unit 126, the receiver unit, 128 and a plurality of bio-medical units 10 equipped to communicate with each other and with the transmitter unit 126 and the receiver unit 128. The bio-medical unit 10 includes an echo receiver 528, the MMW transceiver 138, the power harvesting module 46, the memory 52, and the processing module 50. The echo receiver 528 receives echo signals 530 from an object 526 in accordance with the MRI sequence.

The processing module 50 produces processed echo signals based on the echo signals 530 received by the echo receiver 528. The processing module 50 may determine to share the processed echo signal information with the plurality of bio-medical units 10 based in part on instructions received by the MMW transceiver 138 from the transmitter unit 126. The processing module 50 may produce further processed echo signals based on the shared processed echo signals of the plurality of bio-medical units 10. The processing module 50 may encode and send the further processed echo signal information as MMW outbound signals 150 to the receiver unit 128. The method of processing and communicating the processed echo signals is discussed in greater detail with reference to FIG. 27.

Figure 27:
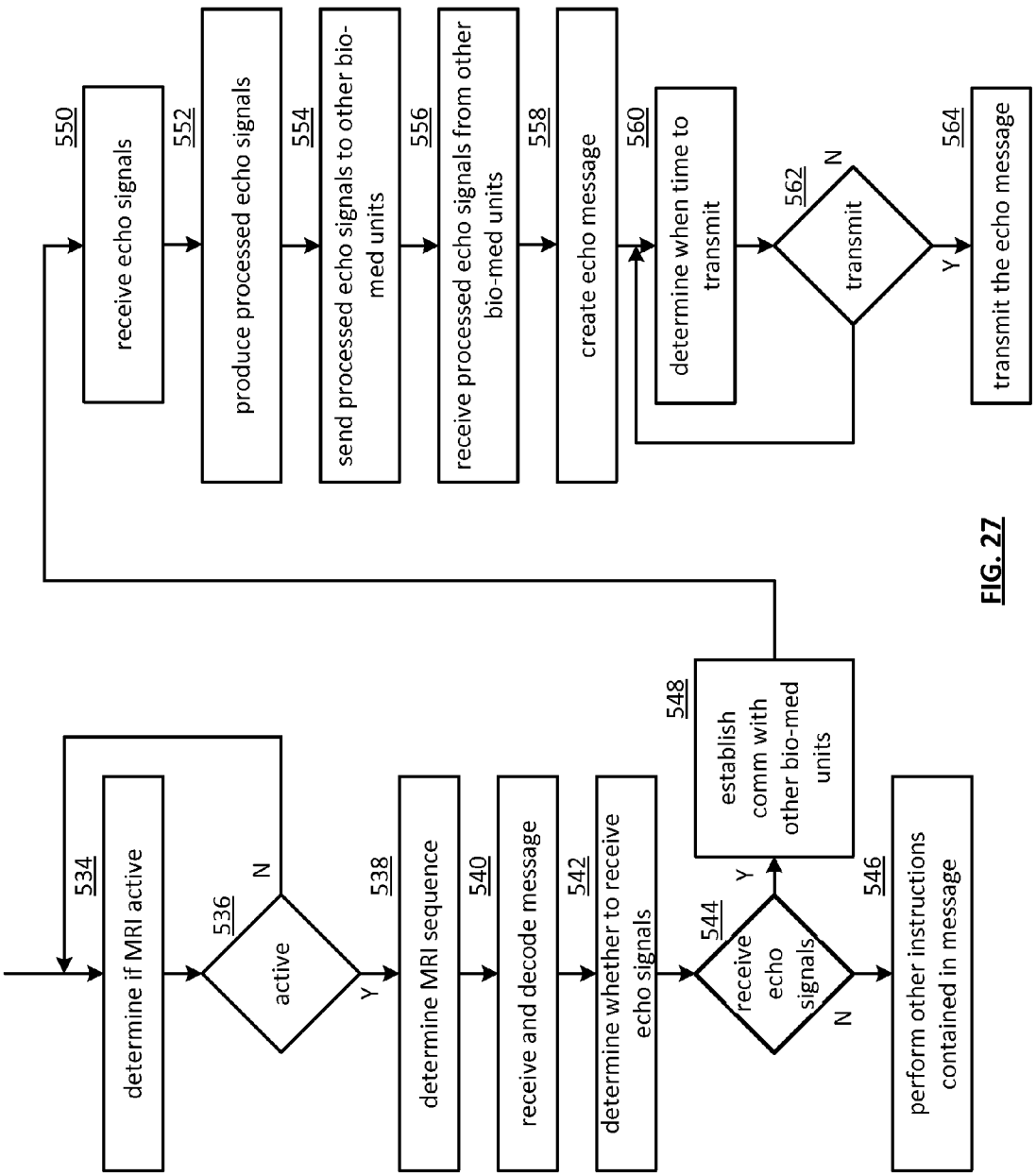
FIG. 27 is a logic diagram of another embodiment of a method for bio-medical unit communications in accordance with the invention.

FIG. 27 is another flowchart illustrating the processing of MRI signals where the processing module 50 of the bio-medical unit 10 may communicate with other bio-medical units 10 to assist the MRI in the reception and processing of MRI EM signals 146. The method begins at step 534 where the processing module 50 determines if the MRI is active based on receiving MRI EM signals 146 via the EM transceiver 174. At step 536, the method branches back to step 534 when the processing module 50 determines that the MRI is not active. For example, the MRI sequence may not start until the processing module 50 communicates to the MRI that it is available to assist. At step 536, the method continues to step 538 when the processing module 50 determines that the MRI is active.

At step 538, the processing module 50 determines the MRI sequence based on received MRI EM signals 146 (e.g., gradient pulses and/or MRI RF pulses). At step 540, the processing module 50 receives EM signals 146 and/or MMW inbound signals 148 in accordance with the MRI sequence and decodes a message for the processing module 50.

At step 542, the processing module 50 determines whether to receive echo signals 530 produced by the MRI sequence based in part on the decoded message. The determination may be based on a comparison of the MRI echo signal data request to the capabilities of the bio-medical unit 10. At step 544, the method branches to step 548 when the processing module 50 determines to receive echo signals 530. At step 544, the method continues to step 546 when the processing module 50 determines to not receive echo signals 530. At step 546, the processing module 50 performs other instructions contained in the message. The method ends.

At step 548, the processing module 50 establishes communications with other bio-medical units 10. The processing module 50 may establish communications with other bio-medical units 10 utilizing MMW communication 532. The processing module 50 may send a receive echo signals command to the other bio-medical units 10 such that the plurality of bio-medical units 10 will all receive subsequent echo signals 530.

At step 550, the processing module 50 receives echo signals 530 via the echo receiver 528. Note the echo signals 530 may comprise EM RF signals across a wide frequency band as reflected off of the object 526 during the MRI sequence. At step 552, the processing module 50 processes the received echo signals 530 to produce processed echo signals. Note that this may be a portion of the overall processing required to lead to the desired MRI imaging.

At step 554, the processing module 50 sends the processed echo signals to other bio-medical units via MMW communication 532. Note that bio-medical units 10 receiving the processed echo signals may re-send the processed echo signals to still other bio-medical units 10. Further note that the one of more of the plurality of bio-medical units 10 may further process the processed echo signals to produce processed echo signals.

At step 556, the processing module 50 may receive the processed echo signals from other bio-medical units via MMW communication 532. Note that the process echo signals may include functional module 54 information including sensor data and location. The processing module 50 may process the processed echo signals to produce processed echo signals (e.g., refined signals, an aggregation, a composite, a result, etc.).

At step 558, the processing module 50 creates an echo message based on the processed echo signals where the echo message contains information about the echo signals 530. At step 560, the processing module 50 determines when it is time to transmit the echo message encoded as MMW outbound signals 150 via MMW communication 532 in accordance with the MRI sequence. For example, the MMW transceiver 138 may transmit MMW outbound signals 150 between any of the MRI sequence steps. For example, the MMW transceiver 138 may transmit MMW outbound signals 150 between specific predetermined steps of the MRI sequence.

At step 562, the method branches back to step 560 when the processing module 50 determines it is not time to transmit the echo message. At step 566, the method continues to step 564 when the processing module 50 determines it is time to transmit the echo message. At step 564, the processing module 50 transmits the echo message encoded as MMW outbound signals.

Figure 28:
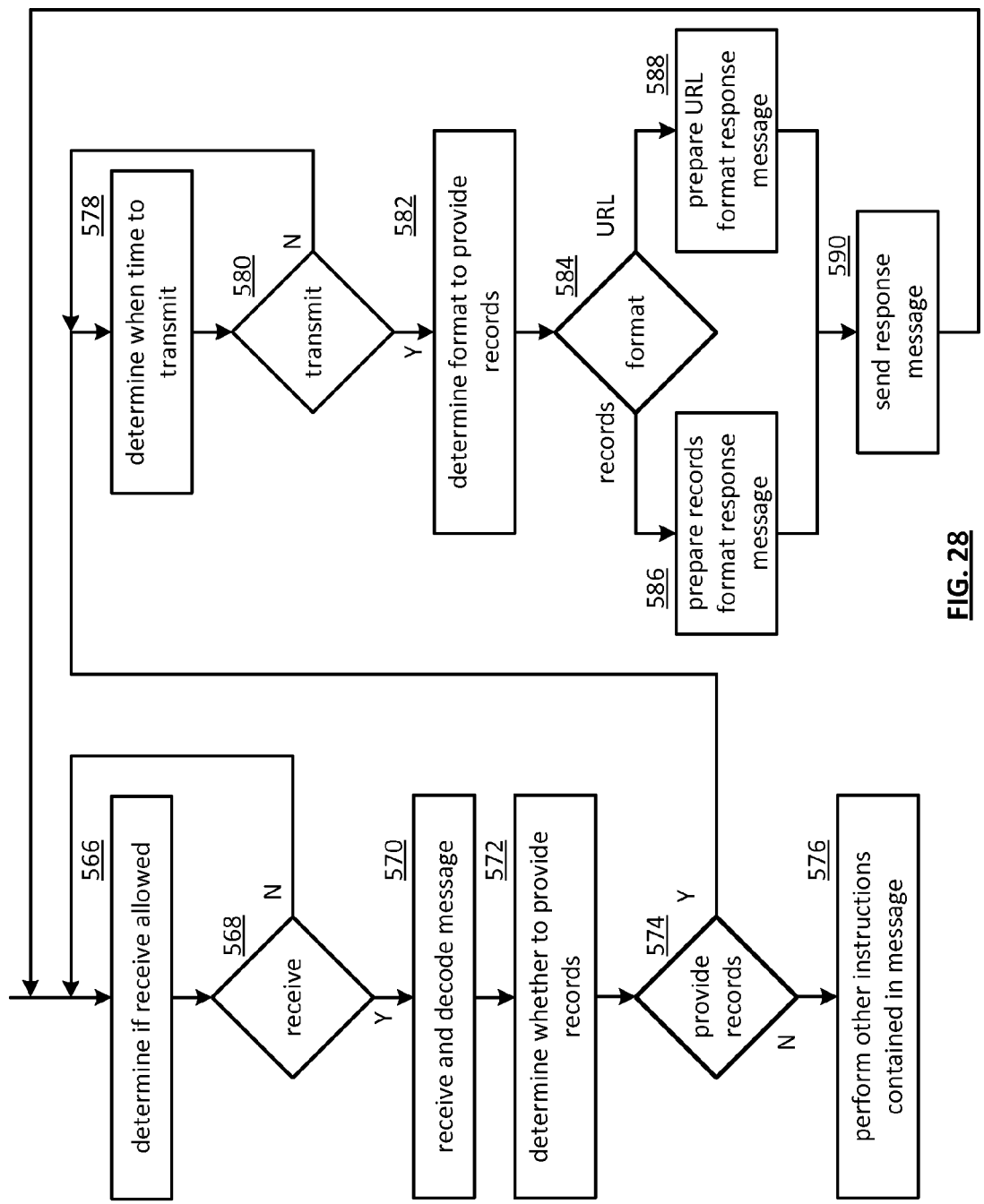
FIG. 28 is a logic diagram of another embodiment of a method for bio-medical unit communications in accordance with the invention.

FIG. 28 is a flowchart illustrating the communication of records where the processing module 50 of the bio-medical unit 10 determines to provide medical records. The method begins at step 566 where the processing module 50 determines if receiving MMW communication is allowed. The determination may be based on one or more of a timer, a command, available power, a priority indicator, and/or interference indicator. For example, the MMW transceiver 138 may receive MMW inbound signals 148 for a 500 millisecond window every 3 minutes.

At step 568, the method branches back to step 566 when the processing module 50 determines that receiving MMW communication is not allowed. At step 568, the method continues to step 570 where the processing module 50 directs the MMW transceiver 138 to receive MMW inbound signals 148. The processing module 50 may decode messages from the MMW inbound signals 148 such that the decoded message include one or more of a status request, a records request, a sensor data request, a processed data request, a position request, a command, and/or a request for MRI echo signal data.

At step 572, the processing module 50 determines whether to provide records in response to the records request based in part on the decoded message. The determination may be based on a comparison of the records request to the capabilities of the bio-medical unit 10. Note that records may include patient history, medications, alerts, allergies, personal information, contact information, age, weight, test results, etc.

At step 576, the method branches to step 578 when the processing module 50 determines to provide records. At step 576, the method continues to step 576 when the processing module 50 determines to not provide records. At step 576, the processing module 50 performs other instructions contained in the message. The method ends.

At step 578, the processing module 50 determines when it is time to transmit. The determination may be based on a timer, a command, available power, a priority indicator, a timeslot, and/or interference indicator. At step 580, the method branches back to step 578 when the processing module 50 determines it is not time to transmit. At step 580, the method continues to step 582 when the processing module 50 determines it is time to transmit.

At step 582, the processing module 50 determines the format to provide records. The format determination may be based on one or more of a memory lookup, a command, available power, the type of records requested, an access ID of the requester, a priority indicator, a level of detail indicator, and/or a freshness indicator. Note that the format may include records format as stored in the bio-medical unit memory (e.g., all or a portion of the records) or a uniform resource locator (URL) to link to another memory in one or more of the service provider's computer, the database, and/or the server.

At step 584, the method branches to step 588 when the processing module 50 determines the format to provide records is the URL format. At step 584, the method continues to step 586 where the processing module 50 prepares the records format response message based on records information retrieved from the bio-medical unit memory 52. The method branches to step 590.

At step 588, the processing module prepares the URL format response message based on retrieving the URL from the bio-medical unit memory 52. At step 590, the processing module 50 transmits the response message encoded as MMW outbound signals 150. For example, the bio-medical unit 10 transmits the response message via a second wireless communications medium including one or more of infrared signals, ultrasonic signals, visible light signals, audible sound signals, and/or EM signals via one or more of the functional modules.

Figure 29:
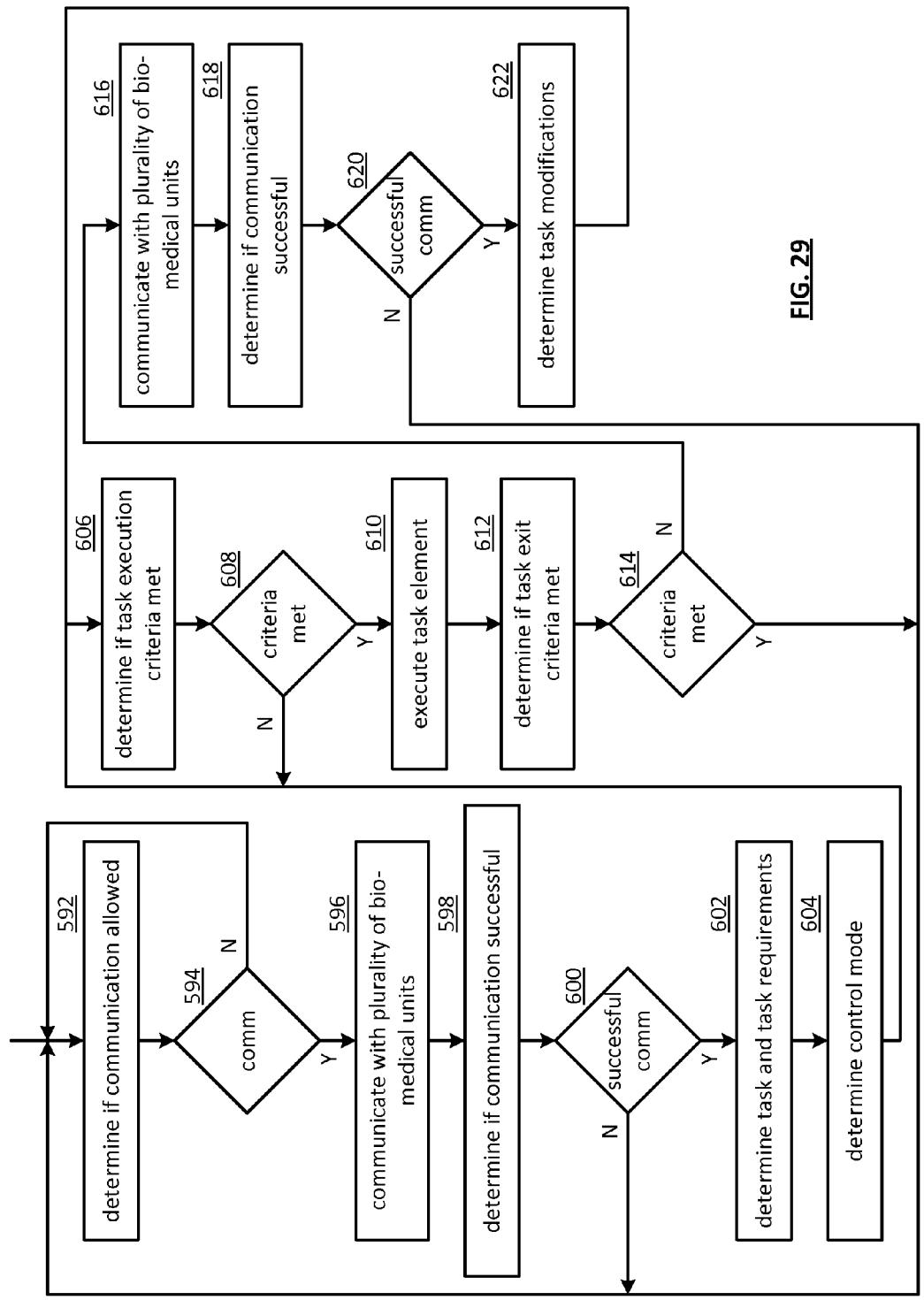
FIG. 29 is a logic diagram of an embodiment of a method for coordination of bio-medical unit task execution in accordance with the present invention.

FIG. 29 is a flowchart illustrating the coordination of bio-medical unit task execution where the processing module 50 determines and executes tasks with at least one other bio-medical unit 10. The method begins at step 592 where the processing module 50 determines if communication is allowed. The determination may be based on one or more of a timer, a command, available power, a priority indicator, an MRI sequence, and/or interference indicator.

At step 594, the method branches back to step 592 when the processing module 50 determines that communication is not allowed. At step 594, the method continues to step 596 when the processing module 50 determines that communication is allowed. At step 596, the processing module 50 directs the communication module 48 to communicate with a plurality of bio-medical units 10 utilizing RF and/or MMW inbound and/or outbound signals. The processing module 50 may decode messages from the RF and/or MMW inbound and/or outbound signals inbound signals. At step 598, the processing module 50 determines if communications with the plurality of bio-medical units 10 is successful based in part on the decoded messages.

At step 600, the method branches back to step 592 when the processing module determines that communications with the plurality of bio-medical units 10 is not successful. Note that forming a network with the other bio-medical units 10 may be required to enable joint actions. At step 600, the method continues to step 602 when the processing module 50 determines that communications with the plurality of bio-medical units 10 is successful.

At step 602, the processing module 50 determines the task and task requirements. The task determination may be based on one or more of a command from a parent bio-medical unit 10, external communications, a preprogrammed list, and/or in response to sensor data. The task requirements determination may be based on one or more of the task, a command from a parent bio-medical unit 10, external communications, a preprogrammed list, and/or in response to sensor data. Note that the task may include actions including one or more of drilling, moving, sawing, jumping, spreading, sensing, lighting, pinging, testing, and/or administering medication.

At step 604, the processing module 50 determines the control mode based on one or more of a command from a parent bio-medical unit 10, external communications, a preprogrammed list, and/or in response to sensor data. Note that the control mode may include autonomous, parent (bio-medical unit), server, and/or peer.

At step 606, the processing module 50 determines if task execution criteria are met based on sensor data, communication with other bio-medical units 10, a command, a status indicator, a safety indicator, a stop indicator, and/or location information. Note that the task execution criteria may include one or more of safety checks, position information of the bio-medical unit 10, position information of other bio-medical units 10, and/or sensor data thresholds.

At step 608, the method branches back to step 606 when the processing module 50 determines that the task execution criteria are not met. At step 608, the method continues to step 610 when the processing module 50 determines that the task execution criteria are met. At step 610, the processing module 50 executes a task element. A task element may include a portion or step of the overall task. For example, move one centimeter of a task to move three centimeters.

At step 612, the processing module 50 determines if task exit criteria are met based on a task element checklist status, sensor data, communication with other bio-medical units 10, a command, a status indicator, a safety indicator, a stop indicator, and/or location information. Note that the task exit criteria define successful completion of the task.

At step 614, the method branches back to step 592 when the processing module 50 determines that the task exit criteria are met. In other words, the plurality of bio-medical units 10 is done with the current task and is ready for the next task. At step 614, the method continues to step 616 when the processing module 50 determines that the task exit criteria are not met.

At step 616, the processing module 50 directs the communication module 48 to communicate with the plurality of bio-medical units 10 utilizing RF and/or MMW inbound and/or outbound. The processing module 50 may decode messages from the RF and/or MMW inbound and/or outbound signals inbound signals. Note that the messages may include information in regards to task modifications (e.g., course corrections). At step 618, the processing module 50 determines if communications with the plurality of bio-medical units 10 is successful based in part on the decoded messages.

At step 620, the method branches back to step 592 when the processing module determines that communications with the plurality of bio-medical units is not successful (e.g., to potentially restart). Note that maintaining the network with the other bio-medical unit may be required to enable joint actions. At step 620, the method continues to step 622 when the processing module determines that communications with the plurality of bio-medical units is successful.

At step 622, the processing module 50 determines task modifications. The task modifications may be based on one or more of a command from a parent bio-medical unit 10, and/or external communications. The task modifications determination may be based on one or more of the task, a command from a parent bio-medical unit 10, external communications, a preprogrammed list, and/or in response to sensor data. The method branches back to step 606 to attempt to complete the current task.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "coupled to" and/or "coupling" and/or includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" indicates that an item includes one or more of power connections, input(s), output(s), etc., to perform one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

The present invention has also been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

What is claimed is:

1. A bio-medical unit for implanting in or on a body, the bio-medical unit comprising:
  a power harvesting module operable to generate a power supply voltage from an electromagnetic signal transmitted from a signal source external to the bio-medical unit; and
  a radio frequency (RF) communication module coupled to the power harvesting module and powered by the power supply voltage, in which the RF communication module is operable to:
    interpret a pattern of the electromagnetic signal to determine null intervals in the electromagnetic signal;
    receive a downstream RF communication signal from a communication device external to the bio-medical unit during at least one of the null intervals;
    convert the downstream RF communication signal into downstream information for processing by the bio-medical unit;
    convert upstream information of the bio-medical unit into an upstream RF communication signal; and
    transmit the upstream RF communication signal to the communication device during one or more of the null intervals.

2. The bio-medical unit of claim 1, wherein the electromagnetic signal comprises: a magnetic resonance imaging (MRI) signal having at least one of a radio frequency (RF) component and a gradient magnetic field component.

3. The bio-medical unit of claim 1 further comprises:
  a processing module operable to:
    convert the downstream information into at least one of downstream data and a downstream instruction for processing; and
    convert at least one of an upstream instruction and upstream data into the upstream information of the bio-medical unit; and
  a function module operable to perform at least one of:

generate the at least one of an upstream instruction and the upstream data; and perform a bio-medical function based on the at least one of downstream data and the downstream instruction.

4. The bio-medical unit of claim 3 further comprises:
the processing module further operable to:
interpret the downstream instruction to determine whether the functional module is to be enabled to receive an echo signal, wherein the echo signal corresponds to the electromagnetic signal reflecting off of an internal portion of the body; and
enable the functional module when the functional module is to be enabled to receive an echo signal;
the functional module is further operable to:
receive the echo signal; and
convert the echo signal into echo information; and
the processing module is further operable to convert the echo information into the upstream information.

5. The bio-medical unit of claim 4, wherein the processing module is further operable to perform at least one of:
passively convert the echo information into the upstream information; and
actively convert the echo information into the upstream information.

6. The bio-medical unit of claim 1, wherein the RF communication module further functions to:
determine whether an electromagnetic function is active;
when the electromagnetic function is active, determine the predetermined pattern;
determine the at least one null interval for receiving the downstream RF communication signal;
determine whether the upstream RF communication is pending; and
determine the one or more of the null intervals, when the upstream RF communication is pending.

7. A bio-medical unit for implanting in or on a body, comprising:
a power harvesting module operable to generate a supply voltage from an electromagnetic signal transmitted from a signal source external to the bio-medical unit; and
a communication module coupled to the power harvesting module and powered by the supply voltage that is generated by the power harvesting module, in which the communication module is operable to determine null intervals in the electromagnetic signal and communicate with a communication device external to the bio-medical unit during one or more of the null intervals.

8. The bio-medical unit of claim 7, wherein the electromagnetic signal is a magnetic resonance imaging (MRI) signal.

9. The bio-medical unit of claim 7, wherein the communication module communicates with the communication device utilizing radio frequency (RF) signals.

10. The bio-medical unit of claim 7, wherein the communication module communicates with the communication device utilizing millimeter wave (MMW) signals.

11. The bio-medical unit of claim 7, wherein the communication module communicates with the communication device utilizing ultrasound signals.

12. The bio-medical unit of claim 7, wherein the communication module communicates with the communication device utilizing optical signals.

13. The bio-medical unit of claim 7, wherein the signal source and the communication device are located within a magnetic resonance imaging (MRI) device.

14. The bio-medical unit of claim 7, wherein the signal source is within a magnetic resonance imaging (MRI) device and the communication device is located at a different location than the MRI device.

15. The bio-medical unit of claim 7 further comprising a processing module coupled to be powered by the supply voltage from the power harvesting module, and the processing module coupled to the communication module to process communication signals received from the communication device.

16. The bio-medical unit of claim 7 further comprising a functional module coupled to be powered by the supply voltage from the power harvesting module, and the functional module coupled to the communication module to respond to communication signals received from the communication device to perform a medical function.

17. The bio-medical unit of claim 7 further comprising:
a processing module coupled to be powered by the supply voltage from the power harvesting module, and the processing module coupled to the communication module to process communication signals received from the communication device; and
a functional module coupled to be powered by the supply voltage from the power harvesting module, and the functional module coupled to the processing module to respond to communication signals processed by the processing module to perform a medical function.

18. A method of communicating with a bio-medical unit implanted in or on a body, comprising:
subjecting the bio-medical unit to an electromagnetic signal transmitted from a signal source external to the bio-medical unit;
utilizing a power harvesting module of the bio-medical unit to harvest energy from the electromagnetic signal to generate a supply voltage;
powering a communication module of the bio-medical unit by use of the supply voltage;
interpreting a pattern of the electromagnetic signal to determine null intervals in the electromagnetic signal;
receiving, in the communication module, a downstream communication signal from a communication device external to the bio-medical unit during at least one of the null intervals; and
processing the downstream communication signal to perform a medical function of the bio-medical unit.

19. The method of claim 18, wherein when subjecting the bio-medical unit to the electromagnetic signal, the electromagnetic signal is a magnetic resonance imaging (MRI) signal.

20. The method of claim 18 further comprising, transmitting an upstream communication signal from the communication module to the communication device during at least one of the null intervals.

* * * * *